US009497919B2

(12) United States Patent
Hirota et al.

(10) Patent No.: US 9,497,919 B2
(45) **Date of Patent: *Nov. 22, 2016**

(54) BARLEY LIPOXYGENASE 1 GENE, SELECTION METHOD FOR BARLEY, MATERIALS FOR MALT ALCOHOLIC BEVERAGES AND METHOD FOR PRODUCTION OF MALT ALCOHOLIC BEVERAGES

(71) Applicant: SAPPORO BREWERIES LIMITED, Tokyo (JP)

(72) Inventors: Naohiko Hirota, Gunma (JP); Takafumi Kaneko, Gunma (JP); Hisao Kuroda, Yaizu (JP); Hirotaka Kaneda, Shizuoka (JP); Kiyoshi Takoi, Yaizu (JP); Kazuyoshi Takeda, Kurashiki (JP)

(73) Assignee: SAPPORO BREWERIES LIMITED, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/662,416

(22) Filed: Mar. 19, 2015

(65) Prior Publication Data

US 2015/0257354 A1 Sep. 17, 2015

Related U.S. Application Data

(63) Continuation of application No. 13/800,500, filed on Mar. 13, 2013, now abandoned, which is a continuation of application No. 13/667,538, filed on Nov. 2, 2012, now abandoned, which is a continuation of application No. 12/505,723, filed on Jul. 20, 2009, now abandoned, which is a continuation of application No. 10/550,528, filed as application No. PCT/JP2004/004217 on Mar. 25, 2004, now Pat. No. 7,897,850.

(30) Foreign Application Priority Data

Mar. 25, 2003 (JP) ................................ 2003-083924

(51) Int. Cl.

| | |
|---|---|
| ***A01H 5/00*** | (2006.01) |
| ***A01H 11/00*** | (2006.01) |
| ***A23L 2/00*** | (2006.01) |
| ***C12H 1/14*** | (2006.01) |
| ***C12C 11/00*** | (2006.01) |
| ***C12N 9/02*** | (2006.01) |
| ***C12P 19/34*** | (2006.01) |
| ***C12C 1/00*** | (2006.01) |
| ***C07H 21/04*** | (2006.01) |
| ***C07K 1/00*** | (2006.01) |
| ***A01H 5/10*** | (2006.01) |
| ***C12Q 1/68*** | (2006.01) |
| ***A23L 2/38*** | (2006.01) |

(52) U.S. Cl.

CPC . *A01H 5/10* (2013.01); *A23L 2/38* (2013.01); *C12C 1/00* (2013.01); *C12N 9/0069* (2013.01); *C12Q 1/6895* (2013.01); *A23V 2002/00* (2013.01); *C12Q 2600/13* (2013.01); *C12Q 2600/156* (2013.01)

(58) Field of Classification Search

CPC ........ A01H 5/10; C12C 1/00; C12N 9/0069; C12Q 2600/156; C12Q 2600/13; C12Q 1/6895; A23L 2/38; A23V 2002/00

USPC .................. 800/320, 295; 426/590, 592, 16; 435/189, 91.1, 93; 536/23.1, 23.2; 530/350

See application file for complete search history.

(56) References Cited

U.S. PATENT DOCUMENTS

| | | | |
|---|---|---|---|
| 7,897,850 | B2 | 3/2011 | Hirota et al. |
| 2003/0167544 | A1 | 9/2003 | Douma et al. |
| 2005/0204437 | A1 | 9/2005 | Breddam et al. |
| 2013/0196027 | A1 | 8/2013 | Hirota et al. |

FOREIGN PATENT DOCUMENTS

| | | |
|---|---|---|
| CA | 2159411 | 3/1996 |
| JP | 2004-290024 | 10/2004 |
| RU | 2 161 419 C2 | 1/2001 |
| WO | 02/053721 | 7/2002 |
| WO | WO 02/053720 | 7/2002 |

OTHER PUBLICATIONS

Kuroda et al. "Characterization of Factors that Transform Linoleic Acid into Di- and Trihydroxyoctadeceonoic Acids in Mash", Journal of Bioscience and Bioengineering, vol. 93, No. 1, pp. 73-77 (2002).

Shibata et al. "Plant Lipoxygenases", J. Lipid Mediators Cell Signalling, vol. 12, pp. 213-228.

Drost et al. Flavor Stability, ASBC Journal, vol. 48, No. 4, pp. 124-228.

Vilarinhos et al. "Use of the Random Amplified Polymorphic DNA Technique to Characterize Soybean (*Glycine max* (L.) Merrill) Genotypes", Rev. Brasil. Genet., vol. 17, No. 3, pp. 287-290 (1994).

Hessler et al. "Association of a Lipoxygenase Locus, Lpx-B1, with Varation in Lipoxygenase Activity in Durum Wheat Seeds", Crop Science, vol. 42, pp. 1695-1700 (2002).

Kobayashi et al. "The Production of Linoleic and Linolenic Acid Hydroperoxides during Mashing", Journal of Fermentation and Bioengineering, vol. 76, No. 5, pp. 371-375.

Kobayshi et al. "A New Method for Evaluating Foam-Damaging Effect by Free Fatty Acids", J. Am. Soc. Brew. Chem., vol. 60, No. 1, pp. 37-41 (2002).

(Continued)

*Primary Examiner* — Ganapathirama Raghu

(74) *Attorney, Agent, or Firm* — Oblon, McClelland, Maier & Neustadt, L.L.P.

(57) ABSTRACT

A barley plant including a mutant LOX-1 protein and that is deficient in lipoxygenase activity.

10 Claims, 15 Drawing Sheets

(56) References Cited

OTHER PUBLICATIONS

Kaneda, et al. "Adsorption to or Desorption of Beer Components from a Lipid Membrane Related to Sensory Evaluation", Journal of Bioscience and Bioengineering, vol. 92, No. 3, pp. 221-226 (2001).

Yasui, Journal of the Brewing Society of Japan, vol. 96, pp. 94-99 (2001).

McElroy, et al., "What's Brewing in Barley Biotechnology?", Bio/Technology, Nature Publishing Co., vol. 13, No. 3, pp. 245-249 (1995).

Kobayashi, et al., "Behavior of Mono-, Di- and Trihydroxyoctadecenoic Acids during Mashing and Methods of controlling Their Production" Journal of Bioscience and Bioengineering, Elsevier, Amsterdam, vol. 90, No. 1, pp. 69-73 (2000).

"Catalogue of Barley Germplasm Preserved in Okayama University 1983", Mar. 30, 1983.

Matthew J. Wishart, et al., A Single Mutation Converts a Novel Phosphotyrosine Binding Domain into a Dual-specificity Phosphatase, The Journal of Biological Chemistry, vol. 270, No. 45, 1995, pp. 26782-26785.

Andrzej Witkowski, et al., Conversion of a β-Ketoacyl Synthase to a Malonyl Decarboxylase by Replacement of the Active-Site Cysteine with Glutamine, Biochemistry, vol. 38, 1999, pp. 11643-11650.

Office Action issued Jun. 25, 2014 in co-pending U.S. Appl. No. 13/667,538.

M:marker,
K: Kendall
S: SBOU 2
→: LOX,
■ 57 Kd Band

S:SBOU 2
K:Kendall

Nucleotide sequences of LOX-1 gene, the regions of 5th intron splicing donor site StuI digest M: Marker,
KC: Kendall cDNA template
SC: SBOU 2 cDNA template
SG: SBOU 2 genomicDNA template M:Marker
F2:Kendall x SBOU 2 F2 DNA AfaI method analysis

Fig. 10

| F2 individual No. | LOX activity | AfaI method CAPS | JBC970 SOUTHERN | | F2 individual No. | LOX activity | AfaI method CAPS | JBC970 SOUTHERN |
|---|---|---|---|---|---|---|---|---|
| 1 | + | KB | KB | | 73 | + | KB | KB |
| 2 | + | KK | KK | | 74 | + | KB | KB |
| 3 | + | KB | KB | | 75 | + | KK | KK |
| 4 | − | BB | KB | | 76 | + | KB | KB |
| 5 | − | BB | BB | | 77 | + | KK | KK |
| 6 | − | BB | BB | | 78 | − | BB | BB |
| 7 | + | KK | KK | | 79 | + | KB | KB |
| 8 | + | KB | KB | | 80 | − | BB | BB |
| 9 | + | KB | KB | | 81 | − | BB | BB |
| 10 | − | BB | BB | | 82 | + | KB | KB |
| 11 | − | BB | KB | | 83 | + | KK | KK |
| 12 | + | KB | KB | | 84 | + | KK | KK |
| 13 | − | BB | BB | | 85 | − | BB | BB |
| 14 | + | KK | KK | | 86 | − | BB | BB |
| 15 | + | KB | KB | | 87 | − | BB | BB |
| 16 | + | KB | KB | | 88 | + | KB | KB |
| 17 | + | KK | KK | | 89 | − | BB | BB |
| 18 | + | KB | KB | | 90 | − | BB | BB |
| 19 | + | KK | KK | | 91 | + | KK | KK |
| 20 | + | KK | KK | | 92 | + | KB | KB |
| 21 | − | BB | KB | | 93 | + | KB | KB |
| 22 | + | KK | KK | | 94 | + | KK | KK |
| 23 | + | KB | KB | | 95 | + | KB | KB |
| 24 | + | KK | KK | | 96 | + | KB | KB |
| 25 | + | KB | KB | | 97 | + | KK | KK |
| 26 | + | KB | KB | | 98 | + | KB | KB |
| 27 | + | KK | KK | | 99 | + | KB | KB |
| 28 | + | KK | KK | | 100 | + | KB | KB |
| 29 | + | KK | KK | | 101 | − | BB | BB |
| 30 | + | KB | KB | | 102 | + | KB | KK |
| 31 | + | KB | KB | | 103 | + | KB | KB |
| 32 | − | BB | KB | | 104 | + | KB | KB |
| 33 | + | KB | KB | | 105 | + | KB | KB |
| 34 | + | KB | KB | | 106 | + | KK | KK |
| 35 | + | KK | KB | | 107 | + | KK | KK |
| 36 | + | KB | KB | | 108 | + | KK | KK |
| 37 | + | KB | KB | | 109 | + | KB | KB |
| 38 | + | KK | KK | | 110 | − | BB | BB |
| 39 | + | KB | − | | 111 | − | BB | BB |
| 40 | + | KB | − | | 112 | + | KB | KB |
| 41 | − | BB | BB | | 113 | + | KB | KB |
| 42 | + | KB | KB | | 114 | + | KB | KB |
| 43 | + | KK | KK | | 115 | − | BB | BB |
| 44 | + | KB | KB | | 116 | + | KB | KB |
| 45 | − | BB | BB | | 117 | − | BB | BB |
| 46 | + | KK | KK | | 118 | + | KK | KK |
| 47 | − | BB | BB | | 119 | + | KB | KB |
| 48 | + | KK | KB | | 120 | + | KK | KK |
| 49 | + | KB | KB | | 121 | + | KB | KB |
| 50 | − | BB | BB | | 122 | + | KB | KB |
| 51 | + | KB | KB | | 123 | + | KK | KK |
| 52 | + | KB | KB | | 124 | + | KB | KB |
| 53 | + | KK | KK | | 125 | − | BB | BB |
| 54 | − | BB | BB | | 126 | + | KK | KK |
| 55 | + | KK | KK | | 127 | + | KB | KB |
| 56 | − | BB | BB | | 128 | + | KB | BB |
| 57 | + | KB | KB | | 129 | + | KB | KB |
| 58 | + | KB | KB | | 130 | + | KB | KB |
| 59 | − | BB | BB | | 131 | + | KK | KB |
| 60 | − | BB | BB | | 132 | + | KK | KK |
| 61 | + | KK | KK | | 133 | − | BB | BB |
| 62 | + | KK | KK | | 134 | − | BB | BB |
| 63 | + | KK | KK | | 135 | + | KK | KK |
| 64 | + | KB | KB | | 136 | + | KB | KB |
| 65 | + | KB | KB | | 137 | + | KB | KK |
| 66 | + | KK | KK | | 138 | + | KB | KB |
| 67 | + | KB | KB | | 139 | − | BB | BB |
| 68 | + | KK | KK | | 140 | + | KK | KK |
| 69 | + | KB | KB | | 141 | + | KB | KB |
| 70 | − | BB | BB | | 142 | + | KB | BB |
| 71 | + | KB | KB | | 143 | + | KK | KK |
| 72 | − | BB | BB | | 144 | + | KB | KB |

M: Marker,
1 and 5:SBOU2、 2:SBOU 5、 3:SBOU 6
4:SBOU 1、 6:SBOU 3、 7:SBOU 4

Fig. 14

| Variety | LOX+F4 | LOX-F4 |
|---|---|---|
| Barley moisture content (%) | 10.9 | 11 |
| Barley weight (g) | 3000 | 3000 |
| Steeping (%) | 44.8 | 44.5 |
| Steeping time (h) | 82 | 82 |
| Malt yield weight (g) | 2571.6 | 2572.2 |
| Malt yield percent (%ad) | 85.7 | 85.7 |
| Malt yield percent (%db) | 90.3 | 90.7 |
| Moisture content (%) | 6.1 | 5.8 |
| Mashing time (min) | 9-15 | 9-15 |
| Lautering speed (min) | 8 | 17 |
| Transparency | 2 | 2 |
| Color (EBC) | 2.1 | 2.2 |
| Boiling color (EBC) | 3.2 | 3.3 |
| Air-dried extract (%) | 67 | 69.3 |
| Anhydrous extract (%) | 71.4 | 73.5 |
| TN (%) | 2.49 | 2.291 |
| SN (%) | 0.648 | 0.645 |
| Crude protein (%) | 15.6 | 14.3 |
| KZ | 26 | 28.1 |
| EVG (%) | 78.8 | 79 |
| DP (°WK) | 348 | 377 |
| DP (WK/TN) | 140 | 165 |
| Viscosity (mPa·s) | 1.87 | 1.89 |
| $\beta$-glucan (mg/l) | 427 | 392 |
| pH | 5.97 | 6 |
| Extract yield (%) | 64.5 | 66.7 |

BARLEY LIPOXYGENASE 1 GENE, SELECTION METHOD FOR BARLEY, MATERIALS FOR MALT ALCOHOLIC BEVERAGES AND METHOD FOR PRODUCTION OF MALT ALCOHOLIC BEVERAGES

CROSS-REFERENCE TO RELATED APPLICATIONS

This application is a continuation application of U.S. Ser. No. 13/800,500 filed Mar. 13, 2013, now abandoned, which is a continuation of U.S. Ser. No. 13/667,538 filed Nov. 2, 2012, now abandoned, which is a continuation of U.S. application Ser. No. 12/505,723 filed Jul. 20, 2009, abandoned, which is a continuation of U.S. application Ser. No. 10/550,528 filed Nov. 27, 2006, now U.S. Pat. No. 7,897,850, which is a 371 of PCT/JP04/04217 filed Mar. 25, 2004 and claims the benefit of JP 2003-083924 filed Mar. 25, 2003.

TECHNICAL FIELD

The present invention relates to a barley lipoxygenase-1 gene, a barley selection method, materials for malt alcoholic beverages and a method for production of malt alcoholic beverages.

BACKGROUND ART

Barley lipoxygenase-1 (hereinafter, "LOX-1") is an enzyme present in malt, which oxidizes malt-derived linoleic acid to 9-hydroperoxyoctadecadienoic acid during mashing for production of malt alcoholic beverages (Kobayashi, N. et al., J. Ferment. Bioeng., 76, 371-375, 1993). 9-Hydroperoxyoctadecadienoic acid is further converted to trihydroxyoctadecenoic acid (THOD) by peroxygenase-like activity (Kuroda, H., et al., J. Biosci. Bioeng., 93, 73-77, 2002). It is known that THOD reduces beer foam stability, imparts an astringent flavor and impairs smoothness of beer flavor (Kobayashi, N., J. Am. Soc. Brew. Chem. 60: 37-41. 2002; and Kaneda, H. et al., J. Biosci. Bioeng., 92, 221-226. 2001), resulting in lower quality of malt alcoholic beverages. In addition, 9-hydroperoxyoctadecadienoic acid is converted to trans-2-nonenal which is the substance responsible for an unpleasant cardboard flavor in aged malt alcoholic beverages (Yasui, Journal of the Brewing Society of Japan, 96:94-99 (2001)).

As a strategy for inhibiting production of trans-2-nonenal in order to improve flavor stability of malt alcoholic beverages, there has been proposed a method of producing malt alcoholic beverages using malt with low LOX-1 activity (Drost, J. Am. Soc. Brew. Chem. 48:124-131 (1990)).

Douma et al. have induced mutation in barley by mutagenic (chemical) treatment to create an induced mutated line exhibiting 9% of lower LOX-1 activity compared to controls, and have attempted to produce malt alcoholic beverages using such barley (WO02/053721).

Even when such barley is used, however, the reduced trans-2-nonenal concentration of the obtained malt alcoholic beverages is insufficient and flavor stability is not adequately improved. Furthermore, absolutely no definite results have been achieved in terms of reducing THOD or improving foam stability.

DISCLOSURE OF INVENTION

The present invention has been accomplished in light of the aforementioned problems of the prior art, and its object is to provide a barley LOX-1 gene which is useful for production of malt alcoholic beverages exhibiting improved flavor stability and foam stability without gene manipulation, a selection method for LOX-1 deficient barley, materials for malt alcoholic beverages derived from barley obtained by the selection method, and a method for production of malt alcoholic beverages using the materials for malt alcoholic beverages.

As a result of much diligent research conducted with the aim of achieving the object described above, the present inventors have completed this invention upon discovering a native barley variety which is completely deficient in LOX-1 activity, and identifying a novel LOX-1 mutant gene from the barley variety.

Specifically, the LOX-1 mutant gene of the present invention is characterized in that the guanine at the splicing donor site (5'-GT-3') of the 5th intron of the known barley LOX-1 gene is mutated to a different base. The different base is preferably adenine.

The selection method for barley LOX-1 deficient barley according to the invention is characterized by distinguishing the barley LOX-1 deficient barley by whether or not the guanine at the splicing donor site of the 5th intron of the LOX-1 gene is mutated to a different base. The different base is preferably adenine.

Also, the selection method for LOX-1 deficient barley is characterized by comprising a genomic DNA extraction step wherein genomic DNA is extracted from a barley sample; a DNA fragment amplification step wherein a DNA fragment containing the splicing donor site of the 5th intron of the LOX-1 gene is amplified from the extracted genomic DNA; and a DNA fragment detection step wherein the DNA fragment containing the splicing donor site of the 5th intron of the LOX-1 gene amplified in the DNA fragment amplification step is cleaved with a restriction enzyme, a DNA fragment having the prescribed number of bases is detected, and the barley LOX-1 deficient barley is distinguished by whether or not the guanine at the splicing donor site is mutated to a different base.

The restriction enzyme used in the DNA fragment detection step is preferably AfaI and/or RsaI which recognize the nucleotide sequence 5'-GTAC-3'.

According to the invention, the barley variety having the LOX-1 activity-deficient trait is distinguished based on the presence or absence of a mutation of guanine at the splicing donor site of the 5th intron of the LOX-1 gene.

As a result, it is possible to easily distinguish the LOX-1 activity-deficient barley variety by analysis on the genetic level, without directly measuring LOX-1 activity. Enzyme activity is influenced by individual growth stages, environment and other factors and is therefore difficult to measure precisely, but this method allows the LOX-1 activity-different barley variety to be distinguished in a different manner from enzyme measurement, and therefore independently of environmental and other factors. Moreover, while enzyme activity cannot be measured until the seeds have matured, DNA screening can identify the presence or absence of the activity-deficient trait at an early stage of growth since it is carried out before flowering, and is thus effective for continuous back-crossing.

The material for malt alcoholic beverages of the invention is characterized by being a seed, a malt, malt extract, barley decomposition product or processed barley derived from barley having a LOX-1 mutant gene according to the invention.

The material for malt alcoholic beverages of the invention is also characterized by being a seed, a malt, malt extract, barley decomposition product or processed barley derived from barley selected by a selection method for LOX-1 deficient barley according to the invention.

The method for production of malt alcoholic beverages of the invention is characterized by using a material for malt alcoholic beverages according to the invention.

According to the invention, it is possible to obtain malt alcoholic beverages with improved flavor stability and foam stability because LOX-1 is not present in the material, and therefore 9-hydroperoxyoctadecadienoic acid is not readily produced from linoleic acid and consequently THOD and trans-2-nonenal are also not readily produced in the malt alcoholic beverage production method.

The invention further provides a nucleic acid comprising the nucleotide sequence from position 1 to 1554 as set forth in SEQ ID NO: 10. This nucleotide sequence represents the coding region of the gene encoding a mutant LOX-1 protein lacking the lipoxygenase activity of LOX-1 protein. By detecting the presence or absence of this nucleic acid in a barley sample, it is possible to distinguish whether or not the barley has the LOX-1 activity-deficient trait.

The invention still further provides a nucleic acid comprising the nucleotide sequence as set forth in SEQ ID NO: 11. This nucleotide sequence represents the genomic sequence of the gene encoding a mutant LOX-1 protein lacking the lipoxygenase activity of LOX-1 protein. By detecting the presence or absence of this nucleic acid in a barley sample, it is possible to distinguish whether or not the barley has the LOX-1 activity-deficient trait.

The invention still further provides a nucleic acid comprising the nucleotide sequence of 10 to 60 continuous bases including the 3178th base in the nucleotide sequence as set forth in SEQ ID NO: 11. The 3178th base is a single nucleotide polymorphism which is Gin authentic LOX-1 and A in mutant LOX-1. By detecting the presence or absence of nucleic acid including the polymorphic site in a barley sample, it is possible to distinguish whether or not the barley has the LOX-1 activity-deficient trait.

The invention still further provides a method for detecting the presence of LOX-1 activity in barley, comprising a step of isolating a genomic DNA from a barley sample, and a step of detecting 3178th base of the nucleotide sequence as set forth in SEQ ID NO: 11, wherein the presence of the base is an indicator of the presence of LOX-1 activity in the barley. According to this method, it is possible to distinguish whether or not tested barley has the LOX-1 activity-deficient trait.

A seed, malt, malt extract, barley decomposition product or processed barley derived from LOX-1 activity-deficient barley discovered by this method may be used as raw material for production of malt alcohol beverages, in order to obtain malt alcoholic beverages with improved flavor stability and foam stability.

BRIEF DESCRIPTION OF DRAWINGS

FIG. 10 is a table summarizing DNA polymorphism in the hybrid 2nd filial generation and LOX activity in the hybrid 3rd filial generation for Kendall.times.SBOU2 in Verification Test 9.

FIG. 14 is a table showing the results of malt analysis of seeds from the LOX+F4 population and LOX-F4 population in Example 5.

BEST MODE FOR CARRYING OUT THE INVENTION

Figure 1:
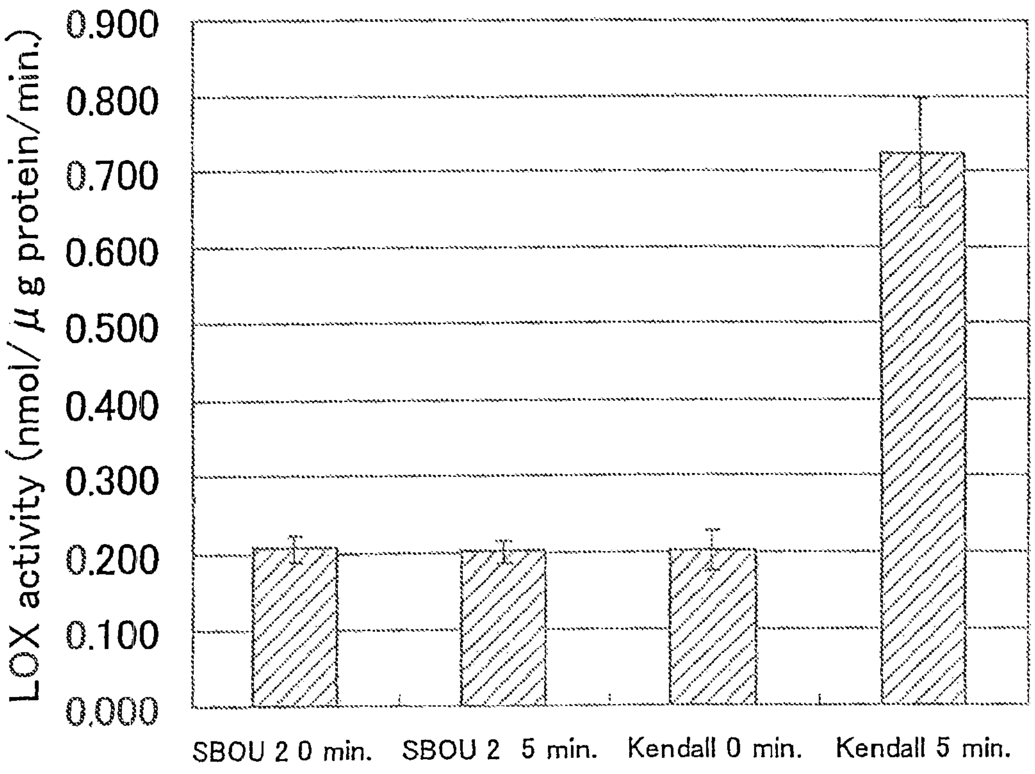
FIG. 1 is a graph showing the results for LOX-1 activity in Search Test 1.

The present invention will now be explained in greater detail.

To begin with, the LOX-1 mutant gene of the invention will be explained.

The LOX-1 mutant gene of the invention is a novel gene discovered by the present inventors, and it is characterized in that the 60th base G of the known barley LOX-1 gene (SEQ ID NO: 1) is replaced by A (SEQ ID NO: 2). Since bases 60-61 of SEQ ID NO: 1 constitute the splicing donor site (5'-GT-3'), this base substitution produces an aberration in LOX-1 splicing so that active LOX-1 cannot be expressed.

The nucleotide sequence of the 5th intron region of the known LOX-1 gene is listed as SEQ ID NO: 1 in the Sequence Listing, and the nucleotide sequence of the portion of the LOX-1 mutant gene of the invention corresponding to the 5th intron region of the LOX-1 gene is listed as SEQ ID NO: 2.

The selection method for LOX-1 deficient barley according to the invention will now be explained.

The selection method for LOX-1 deficient barley according to the invention is characterized by distinguishing barley LOX-1 deficient barley based on whether or not the guanine at the splicing donor site of the 5th intron of the LOX-1 gene is mutated to a different base.

The method for selecting LOX-1 deficient barley utilizing the aforementioned base mutation may be for example, a method of using a primer containing the aforementioned mutation site either at the 3' end of the primer sequence or within the primer sequence for amplification of DNA, detecting the base mutation based on the presence of amplification or on the amplification efficiency and selecting the LOX-1 deficient barley, or a method of amplifying a DNA fragment containing the aforementioned mutation site, determining the nucleotide sequence to detect the base mutation and selecting the LOX-1 deficient barley.

There are no particular restrictions on the method of detecting the nucleotide sequence mutation so long as the method allows detection of DNA fragments, but suitable methods to be employed include agarose gel electrophoresis and polyacrylamide gel electrophoresis. When the DNA mutation is to be detected based on the presence of amplification or on amplification efficiency, quantitative PCR such as the TAQMAN method may be used instead of electrophoresis.

The selection method for LOX-1 deficient barley of the present invention is characterized by comprising, preferably, a genomic DNA extraction step wherein genomic DNA is extracted from a barley sample, a DNA fragment amplification step wherein a DNA fragment containing the splicing donor site of the 5th intron of the LOX-1 gene is amplified from the extracted genomic DNA, and a DNA fragment detection step wherein the DNA fragment containing the splicing donor site of the 5th intron of the LOX-1 gene amplified in the DNA fragment amplification step is cleaved with a restriction enzyme, a DNA fragment having the prescribed number of bases is detected, and the barley LOX-1 deficient barley is distinguished by whether or not the guanine at the splicing donor site is mutated to a different base.

The genomic DNA extraction step of the invention will be explained first.

There are no particular restrictions on the method of extracting the genomic DNA from the barley test sample, and any publicly known method may be employed. Specifically, the extraction may be carried out by, for example, the CTAB method (Murray et al., 1980, Nucleic Acids Res. 8:4321-4325) or the ethidium bromide method (Varadarajan and Prakash 1991, Plant Mol. Biol. Rep. 9:6-12). The tissue used for extraction of the genomic DNA is not limited to barley seeds, but may also be leaves, stems, roots or the like. For example, leaves may be utilized for selection of a lot of individuals in back-crossing generations.

The DNA fragment amplification step of the invention will now be explained.

There are no particular restrictions on the method of amplifying the DNA fragment, and for example, the PCR (Polymerase Chain Reaction) method may be employed. The primers used for the PCR method are not particularly restricted in their nucleotide sequences so long as they are of a region allowing amplification of a DNA fragment containing the splicing donor site of the 5th intron of the LOX-1 gene, and specifically, they are preferably 10-60 continuous bases and more preferably 15-30 continuous bases of the LOX-1 gene. Generally, the nucleotide sequence of the primer will preferably have a GC content of 40-60%. Also, the difference in the Tm values of the two primers used for the PCR method is preferably zero, or very small. The primers preferably do not form a secondary structure with each other.

The DNA fragment detection step of the invention will now be explained.

The LOX-1 mutant gene according to the invention has a different nucleotide sequence from the known LOX-1 as explained above, and therefore if a restriction enzyme which recognizes or cleaves the differing portion is used to cleave the amplification product, a difference in the sizes of the obtained DNA fragments will be apparent. There are no particular limitations on the restriction enzyme used for the invention so long as it recognizes or cleaves the differing portion, but restriction enzymes AfaI and/or RsaI, which have already been demonstrated to exhibit such activity, are preferred.

In other words, since the LOX-1 mutant gene of the invention has the guanine at the splicing donor site mutated to a different base, it lacks the cleavage site for restriction enzymes AfaI and RsaI (5'-GTAC-3': nucleotides 60-63 of the 5th intron) which are present in the known LOX-1 gene. As a result, its cleavage pattern when the gene amplification product containing the cleavage site is cleaved with AfaI and/or RsaI will differ from that of the known LOX-1 gene, thereby allowing identification of the LOX-1 mutant gene.

The DNA fragment having the prescribed number of bases is not limited in its number of bases so long as it is a DNA fragment wherein the presence of the differing portion results in a difference in the size of the DNA fragment obtained by cleaving the amplification product with the restriction enzyme.

The detection in this step is not particularly restricted so long as it is a method allowing detection of the DNA fragment cleaved by the restriction enzyme, and specifically, the detection may be accomplished by agarose gel electrophoresis or polyacrylamide gel electrophoresis, for example.

The material for malt alcoholic beverages of the invention will now be explained.

The material for malt alcoholic beverages of the invention is characterized by being a seed, a malt, malt extract, barley decomposition product or processed barley derived from barley having the LOX-1 mutant gene according to the invention, and by being a seed, a malt, malt extract, barley decomposition product or processed barley derived from barley selected by a selection method for LOX-1 deficient barley according to the invention.

Malt extract is the extract from malt, and as examples there may be mentioned the extract of sugar components or protein components from malt. Barley decomposition product is the product of decomposition of barley with enzymes or the like, and it includes barley mash and the like. Processed barley refers to the milled barley used as the adjunct for malt alcoholic beverages.

Since the material for malt alcoholic beverages according to the invention contains no LOX-1, production of 9-hydroperoxyoctadecadienoic acid from linoleic acid does not readily occur, and consequently production of THOD and trans-2-nonenal also does not readily occur, during the malt alcoholic beverage production method; it is therefore possible to obtain malt alcoholic beverages with improved flavor stability and foam stability.

The method for production of malt alcoholic beverages will now be explained.

The method for production of malt alcoholic beverages of the invention is characterized by using a material for malt alcoholic beverages according to the invention.

The malting step according to the invention will be explained first.

The malting step according to the invention is a malt obtaining step characterized by using LOX-1 deficient barley, and the method is not particularly restricted and may be a publicly known method. More specifically, for example, steeping to a steeping degree of 40-45% is followed by germination at 10-20° C. for 3-6 days and kiln-drying to obtain malt.

The mashing step according to the invention will now be explained.

The mashing step according to the invention is a step of obtaining wort by mashing of the aforementioned malt. More specifically, it consists of the following four steps.

The first step is a mashing step in which the malt-containing material is mixed with water, the obtained mixture is heated for mashing of the malt, and the wort is obtained from the saccharified malt.

The malt used for this step is preferably obtained by addition of water and air to barley for germination followed by drying to remove the radicles. The malt is the source of the necessary enzymes for production of wort, as well as the major starch source as the material for mashing. Also, kiln-dried germinated malt is used for production of the wort in order to impart the characteristic flavor and color of a malt alcoholic beverage. In addition to such malt, there may be added adjuncts such as LOX-1 deficient barley according to the invention and/or ordinary barley, corn starch, corn grits, rice, saccharides or the like.

In the wort production step described above, malt extract, barley decomposition product or processed barley prepared from the LOX-1 deficient barley of the invention and/or ordinary barley is mixed with the mashing water, and the aforementioned adjuncts are added as necessary, to obtain the wort.

The malt is mixed after addition to the mashing water. When adjuncts are also added, they may be also mixed in at this point. Saccharides may be added prior to the boiling described hereunder. There are no particular restrictions on the mashing water, and water may be used which is suitable for the malt alcoholic beverage to be produced. The mashing may be carried out basically under conventional conditions. After lautering of the malt mash obtained in this manner, materials which impart flavoring or bitterness such as hops or herbs are added and the mixture is boiled and then chilled to obtain a chilled wort.

The second step is a step of adding yeast to the chilled wort for fermentation to obtain intermediate products of a malt alcoholic beverage.

The yeast used in this step may be any brewer's yeast for alcohol fermentation, which metabolizes sugars in wort obtained by malt mashing to produce alcohol and carbon dioxide gas, and specifically there may be mentioned, for example, *Saccharomyces cerevisiae* and *Saccharomyces uvarum*.

The fermentation is accomplished by cooling the wort obtained in the mashing step and adding the yeast thereto. The fermentation conditions may be basically the same as for conventional fermentation, and for example, the fermentation temperature will ordinarily be no higher than 15° C. and preferably 8-10° C., while the fermentation period is preferably 8-10 days.

The third step is a storage step in which the intermediate products of the malt alcoholic beverage obtained in the fermentation step is stored.

In this step, the fermentation solution which has completed alcoholic fermentation is transferred to a sealed tank and stored. The secondary fermentation is basically the same as conventional conditions, and for example, the storing temperature is preferably 0-2° C. and the storing time is preferably 20-90 days. Storage of the fermented solution allows re-fermentation and maturation of the residual extract to occur.

The fourth step is a filtering step in which the intermediate products of the malt alcoholic beverage obtained in the storage step is filtered to obtain a malt alcoholic beverage.

The filtering conditions are basically the same as conventional conditions and for example, the filtering material used may be diatomaceous earth, PVPP (polyvinyl pyrrolidone), silica gel, cellulose powder or the like, and the temperature may be 0±1° C.

This procedure yields a malt alcoholic beverage. The filtered malt alcoholic beverage is then tanked, barreled, bottled or canned for shipping to the market, either directly or after sterile filtration or heat treatment.

The proportion of malt used for production of the barley alcoholic beverage is not particular restricted, and the alcoholic beverage may be any one produced using malt as the material. Specifically there may be mentioned, for example, beer and sparkling malt liquor. Non-alcoholic beer and non-alcoholic sparkling malt liquor are also considered malt alcoholic beverages since the production method employed is similar to malt alcoholic beverages such as beer.

Since the material according to the invention contains no LOX-1, production of 9-hydroperoxyoctadecadienoic acid from linoleic acid does not readily occur, and consequently production of THOD and trans-2-nonenal is inhibited, during the malt alcoholic beverage production method, and it is therefore possible to obtain malt alcoholic beverages with improved flavor stability and foam stability.

The nucleic acid and the method for detecting the presence of LOX-1 activity in barley according to the invention will now be explained.

Figure 5:
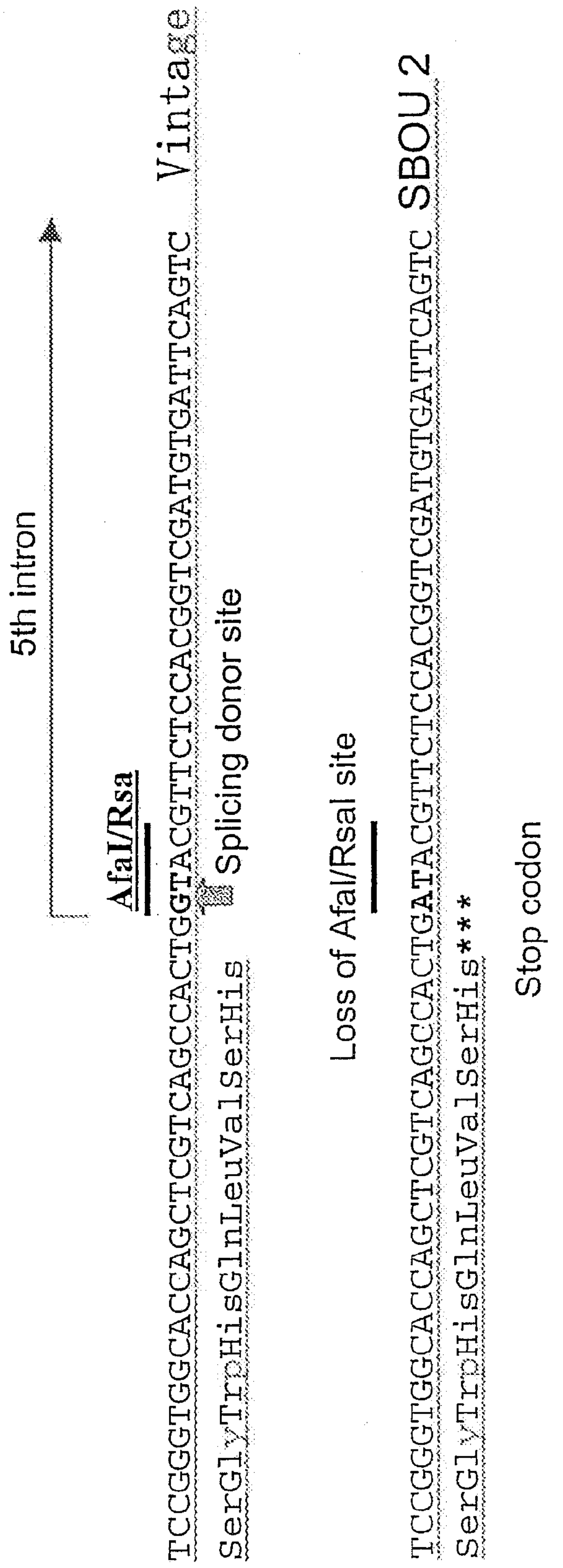
FIG. 5 is a diagram showing the structure of the splicing donor site of the 5th intron of the LOX-1 gene in Verification Test 4 (Vintage is SEQ ID NO:12, SBOU2 is SEQ ID NO:13, and the amino acid sequence is SEQ ID NO:14).

The nucleic acid of the invention is characterized by comprising the nucleotide sequence as set forth in SEQ ID NO: 11. SEQ ID NO: 11 represents the genomic sequence for mutant LOX-1 in the LOX-1 activity-deficient barley variety SBOU2. That is, the LOX-1 mutant gene of the invention is characterized by being represented by SEQ ID NO: 11. The base corresponding to position 3178 is G in the authentic LOX-1 gene, whereas the 3178th base is mutated to A in the mutant LOX-1 gene. This base is also the first base of the 5th intron of the authentic LOX-1 gene, and the sequence GT as the sequence of bases 3178-3179 corresponds to the splicing donor site (FIG. 5). In the mutant LOX-1 gene, however, the sequence of bases 3178-3179 corresponding to the splicing donor site is AT, and therefore a splicing aberration occurs which prevents splicing. Furthermore, the sequence of bases 3176-3178 is TGA which is a stop codon, and therefore translation ends at this point.

Since the mutant LOX-1 protein expressed from the mutant LOX-1 gene only possesses the portion corresponding up to the 5th exon, it lacks the amino acid residues at the C-terminal end from the 5th exon of authentic LOX-1 protein. The molecular weight of authentic LOX-1 protein is 95 kD, while that of the mutant LOX-1 protein is 57 kD. The mutant LOX-1 protein is deficient in lipoxygenase activity, and this correlates with the known fact that the domain corresponding to the exon region near the 5th intron in authentic LOX-1 protein is the active center of plant LOX (Shibata and Axelrod (1995) J. Lipid Mediators and Cell Signaling 12:213-218).

Consequently, if barley possessing the mutant LOX-1 gene is used as raw material for production of malt alcohol beverages, no LOX-1 protein will be present in the raw material, and hence production of 9-hydroperoxyoctadecadienoic acid from linoleic acid during the production method for malt alcoholic beverages will be reduced so that, as a result, inhibition of THOD and trans-2-nonenal production may be achieved in order to obtain malt alcoholic beverages with improved flavor stability and foam stability. Thus, nucleic acid comprising the nucleotide sequence as set forth in SEQ ID NO: 11 according to the invention is highly useful for obtaining malt alcoholic beverages with improved flavor stability and foam stability.

The nucleic acid of the invention provides nucleic acid comprising the nucleotide sequence of 10 to 60 continuous bases including the 3178th base in the nucleotide sequence as set forth in SEQ ID NO: 11. The nucleic acid may be used as a probe to distinguish between authentic and mutant forms of the barley LOX-1 gene. That is, since the 3178th base of the authentic LOX-1 gene is G, the resulting mismatch may be utilized to distinguish between the authentic and mutant forms based on the difference in hybridization. For example, by forming hybrids between these nucleic acids and nucleic acid of the LOX-1 gene, gradually increasing the temperature and measuring the melting temperature of the hybrids, it is possible to easily distinguish between the authentic LOX-1 gene and mutant LOX-1 gene since their melting temperatures will differ. The nucleic acid may also be utilized to distinguish between LOX-1 gene forms (authentic/mutant forms) by methods known to those skilled in the art. From the standpoint of specificity, the nucleic acid preferably comprises a nucleotide sequence of 20-50 continuous bases including the 3178th base, and it preferably includes bases 3178-3181. The nucleic acid may also be labeled with a fluorescent substance, radioisotope or the like.

The method for detecting the presence of LOX-1 activity in barley according to the invention comprises a step of isolating a genomic DNA from a barley sample, and step of detecting 3178th base of the nucleotide sequence as set forth in SEQ ID NO: 11, wherein the presence of the base is an indicator of the presence of LOX-1 activity in the barley. According to this method, it is possible to distinguish whether or not tested barley has the LOX-1 activity-deficient trait.

The barley sample is not restricted to barley seeds, and it may be barley leaves, stems, roots or the like. The nucleic acid may be isolated by a publicly known method, and for example, the CTAB method or the ethidium bromide method may be used.

Detection of the 3178th base of the nucleotide sequence as set forth in SEQ ID NO: 11 may be accomplished by a method known to those skilled in the art. If necessary, for example, a nucleic acid containing the 3178th base of the nucleotide sequence represented by SEQ ID NO: 11 may be amplified by a nucleic acid amplification method such as PCR. The identity of the base at position 3178 of isolated nucleic acid or an amplified nucleic acid fragment can be discriminated, for example, by using nucleic acid comprising the nucleotide sequence represented by SEQ ID NO: 11 wherein the nucleic acid comprises a sequence of 10-60 continuous bases including the 3178th base, as described above.

However, a method for detecting the 3178th base utilizing the difference in bases 3178-3181 of the LOX-1 gene is more convenient and efficient. The site of bases 3178-3181 is the cleavage site for restriction enzymes AfaI/RsaI in the authentic LOX-1 gene, but because the 3178th base is A in the mutant LOX-1 gene, it does not form a cleavage site for restriction enzymes AfaI/RsaI (FIG. 5). In other words, if an isolated nucleic acid or amplified nucleic acid fragment is treated with restriction enzymes AfaI/RsaI, the nucleic acid of authentic LOX-1 will be cleaved whereas nucleic acid of mutant LOX-1 will not be cleaved. Electrophoretic analysis of the restriction enzyme-treated nucleic acid sample will allow the form of the LOX-1 gene (authentic or mutant) to be distinguished based on the difference in electrophoresis patterns, so that the identity of the base at position 3178 can be discriminated. In addition, by using nucleic acid comprising a nucleotide sequence of 10-60 continuous bases including bases 3178-3181 as a probe for hybridization with the restriction enzyme-treated nucleic acid, it is possible to distinguish the form of the LOX-1 gene and thus allow the identity of the 3178th base to be discriminated.

If, as a result of discriminating the 3178th base in this manner, the base is found to be G, then it may be concluded that the tested barley has LOX-1 activity and is not suitable as a raw material for malt alcoholic beverages with improved flavor stability and foam stability. On the other hand, if the base is A, then it may be concluded that the tested barley does not have LOX-1 activity and is therefore suitable as a raw material for malt alcoholic beverages with improved flavor stability and foam stability.

The nucleic acid of the invention is also characterized by comprising the nucleotide sequence from position 1 to 1554 as set forth in of SEQ ID NO: 10. SEQ ID NO: 10 represents the cDNA sequence for mutant LOX-1 expressed by the LOX-1 activity-deficient barley variety SBOU2. The nucleotide sequence from position 1 to 1554 represents the coding region. As explained above, the mutant LOX-1 protein encoded by this cDNA lacks the amino acid residues at the C-terminal end from the 5th exon of authentic LOX-1 protein, its molecular weight is 57 kD, and it lacks lipoxygenase activity.

Consequently, barley expressing this nucleic acid may be used as raw material for production of malt alcohol beverages, in order to obtain malt alcoholic beverages with improved flavor stability and foam stability, as mentioned above.

EXAMPLES

The present invention will now be explained in greater detail through the following examples, with the understanding that these examples are in no way limitative on the invention.

Search Test 1 (Search for LOX-1 Deficient Barley by LOX-1 Enzyme Activity Measurement)

LOX-1 enzyme activity was measured by the method described below, and a search for LOX-1 deficient barley was conducted from barley gene resources.

First, a crude enzyme solution was extracted from barley seeds by the following method. One mature barley seed was crushed with a hammer, and 500 μL of extraction buffer (0.1 M sodium acetate buffer (pH 5.5)) was used for extraction with shaking at 4° C. for 30 minutes. The obtained extract was centrifuged for 10 minutes at 15,000 rpm, and then the supernatant was taken as a crude enzyme solution.

Next, 5 μL of substrate solution (40 mM linoleic acid, 1.0% (W/V) Tween20 aqueous solution) and 85 μL of extraction buffer were added to 10 μL of the crude enzyme solution and mixed therewith, and then reaction was conducted at 24° C. for 5 minutes. The reaction was terminated by adding and mixing 100 μL of stop solution (80 mM 2,6-di-t-butyl-p-cresol, methanol solution). After allowing the reaction mixture to stand at −20° C. for 30 minutes, it was centrifuged at 3000 rpm for 20 minutes and the supernatant was used in the following color developing reaction. A 200 μL portion of a color developing solution (4 mM 2,6-di-t-butyl-p-cresol, 25 mM sulfuric acid, 0.25 mM ammonium iron(II) sulfate hexahydrate, 100 μL xylenol orange, 90% aqueous methanol) was added to 20 μL of the obtained supernatant, and after standing for 30 minutes, the absorbance at 550 nm was measured. As a negative control, reaction was conducted in the same manner using the crude enzyme solution heat treated at 100° C. for 5 minutes for inactivation of LOX-1, while as a positive control there were used seeds of Kendall, a barley variety.

As shown in FIG. 1, the search for gene resources revealed no significant LOX-1 activity in SBOU2 seeds. Since SBOU2 is a landrace, it is a spontaneous mutant rather than a artificially mutagenized line.

Verification Test 1 (Confirmation of Lack of LOX-1 Inhibiting Activity in SBOU2 Crude Enzyme Solutions)

SBOU2 crude enzyme solutions were examined for the presence or absence of LOX-1 inhibiting activity.

Figure 2:
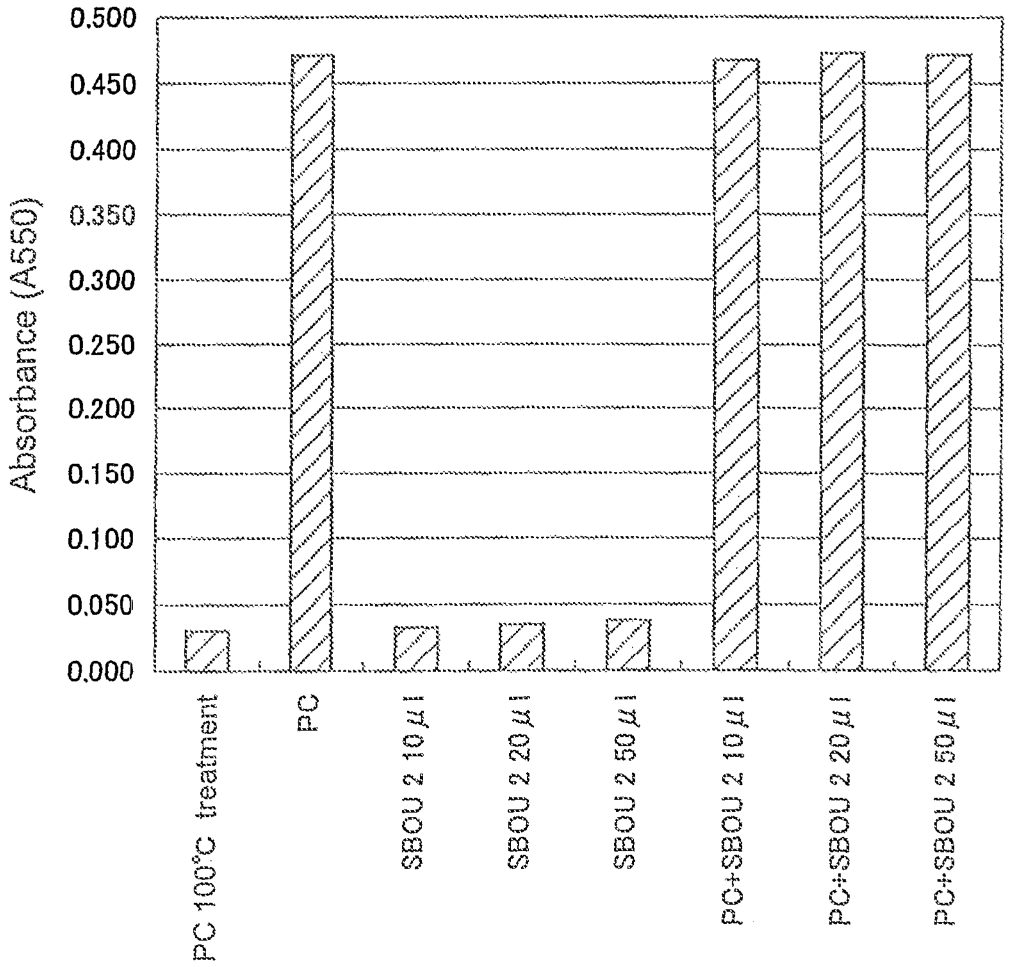
FIG. 2 is a graph showing the results for LOX-1 inhibiting activity in Verification Test 1.

SBOU2 crude enzyme solutions (10 μL, 20 μL, 50 μL) were added to a crude enzyme solution exhibiting LOX-1 activity (positive control: PC) and the changes in LOX-1 activity were examined. The LOX-1 activity was unchanged with addition of the SBOU2 crude enzyme solution, and therefore no LOX-1 inhibiting activity was exhibited by the SBOU2 crude enzyme solutions (FIG. 2). This suggested that the cause of LOX-1 activity deficiency in SBOU2 was not due to a LOX activity-inhibiting substance.

Verification Test 2 (Confirmation of LOX-1 Protein Expression Level in SBOU2 Seeds)

Anti-LOX-1 antibody was used to determine whether or not LOX-1 protein is expressed in SBOU2 seeds.

An anti-LOX-1 antibody was prepared first. The LOX-1 protein used as the antigen was obtained by purifying LOX-1 protein expressed by *E. coli* (Kuroda et al. (2002) J. Bioscience and Bioengineering 93:73-77). The purified protein was used to immunize rabbits for production of LOX-1 antibody. This antibody recognizes both LOX-1 and LOX-2.

Figure 3A:
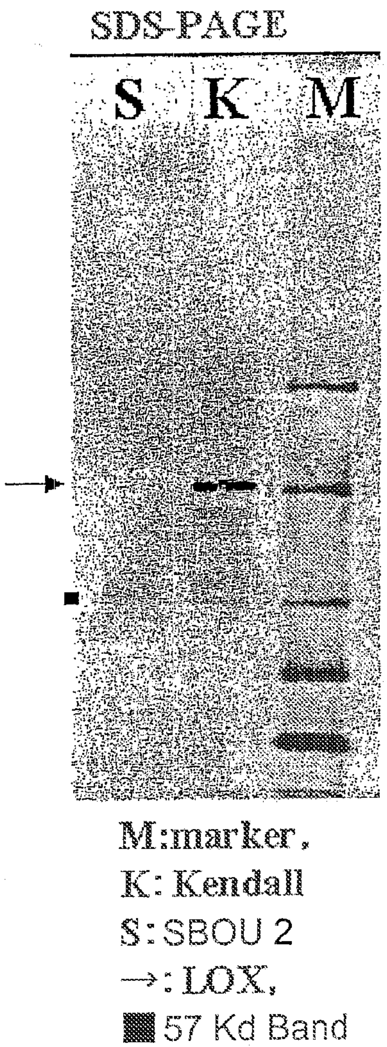
FIGS. 3A and 3B are a pair of electrophoresis images showing the results for Western analysis of barley seed LOX protein in Verification Test 2. Image A shows the results of Western analysis after SDS-PAGE, and B shows the results of Western analysis after IEF.

Western blotting was then carried out in the following manner to examine LOX-1 protein expression in SBOU2 seeds. A 3 μg portion of total soluble protein extracted from SBOU2 using 0.1 M sodium acetate buffer (pH 5.5) was fractionated by SDS-polyacrylamide gel electrophoresis (SDS-PAGE) and then blotted on a PVDF membrane (Millipore). The membrane was rinsed with TTBS (20 mM Tris-HCl (pH 7.5), 0.15 M sodium chloride, 0.05% (w/v) Tween20, 0.05% (w/v) sodium azide) and subsequently reacted with a LOX-1 antibody solution (1000-fold dilution/TTBS) for 30 minutes. The membrane was rinsed with TTBS three times for 5 minutes each time, after which reaction was conducted for 30 minutes with alkali phosphatase-labeled goat anti-rabbit IgG antibody solution (Santa Cruz Biotechnology, TTBS solution at 1000-fold dilution). After rinsing the membrane with TTBS for 5 min.times.2 and then with AP9.5 (10 mM Tris-HCl (pH 9.5), 0.1 M sodium chloride, 5 mM magnesium chloride) for 5 min.times.1, reaction was conducted with alkali phosphatase substrate solution (1 mg/ml nitroblue tetrazolium, 0.5 mg/ml BCIP, AP9.5 solution) for color development. As a result, a dark band with a molecular weight of about 95 kD was obtained with the control variety (Kendall), while two very faint bands were detected at molecular weight regions of about 95 kD and about 57 kD with the SBOU2 seeds (FIG. 3A).

Figure 3B:
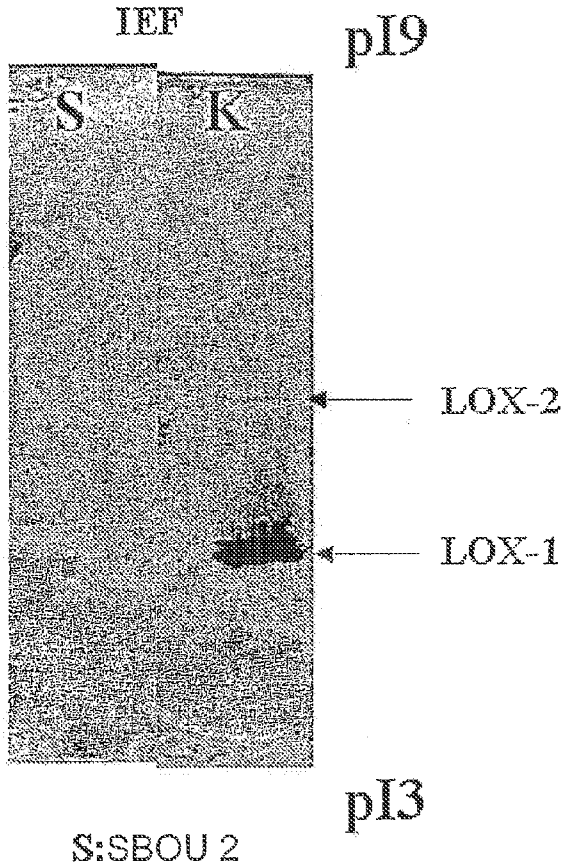

The extraction sample was then subjected to isoelectric focusing (IEF, pI 3-9) using a PhastSystem (Amersham Pharmacia) and subjected to Western analysis in the same manner as above. As a result of analysis with SBOU2, a band was detected at the pI position of LOX-2, but no clear band was present at the pI position of LOX-1 (FIG. 3B). This suggested that the approximately 95 kD band appearing with the SBOU2 seed-extracted protein was LOX-2 protein.

These results confirmed that SBOU2 seeds express virtually no authentic LOX-1 protein.

Verification Test 3 (Analysis of SBOU2 Seed LOX-1 RNA)

RT-PCR was carried out using as the template total RNA extracted from SBOU2 approximately 4-week ripened seeds and 3-day germinated seeds. The reaction was conducted using commercially available kits (Roche Diagnostics, Perkin Elmer), according to the kit manuals. The primers were 5'-GGAGAGGAGGCCAAGAACAAGATG-3' (SEQ ID NO: 3) and 5'-GGTTGCCGATGGCTTAGAT-3' (SEQ ID NO: 4), designed based on the published sequence (DNA Databank: Accession No. L35931). After incubation at 94° C. for 2 min, PCR was carried out with reaction at 94° C., 1 min, 60° C., 2 min and 72° C., 4 min, repeated 31 times, followed by extension reaction at 72° C., 7 min.

Figure 4:
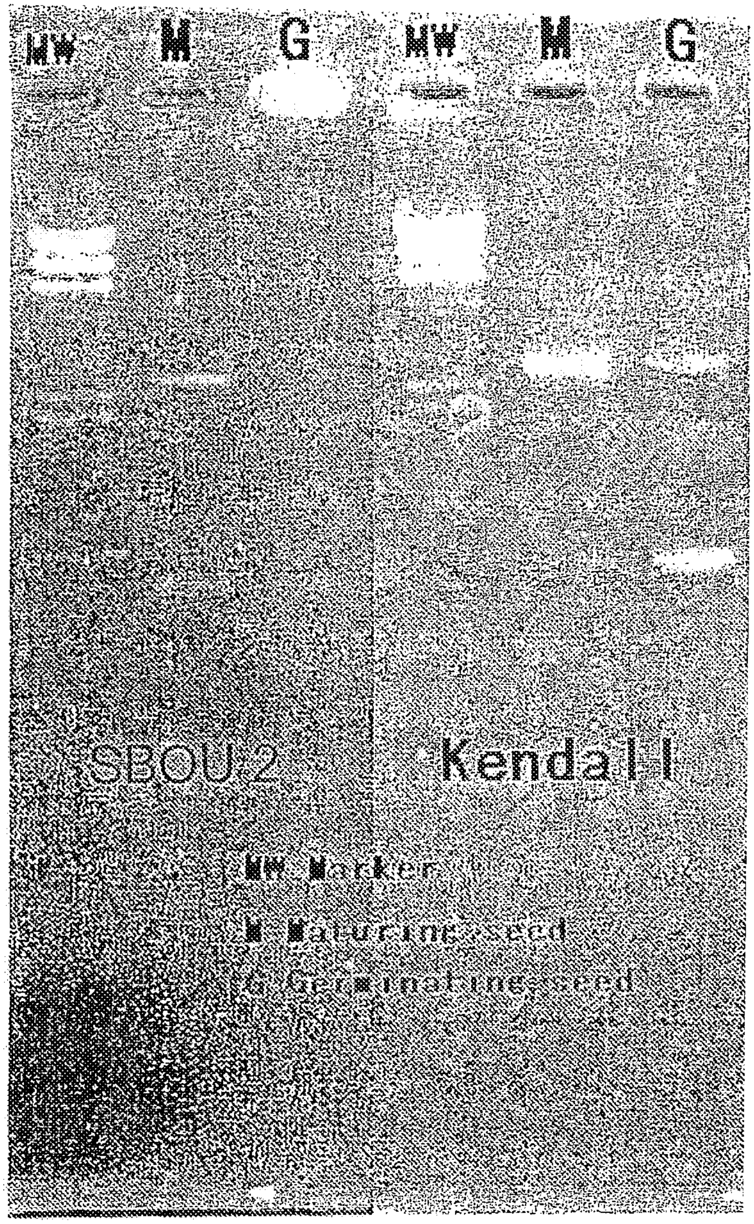
FIG. 4 is an electrophoresis image showing the results for RT-PCR analysis of barley seed RNA in Verification Test 3.

Upon electrophoresis of the amplified DNA, amplification of an approximately 2.5 Kb band was detected for the RNA from the maturing and germinating seeds, although at a slightly lower amount than the control (Kendall variety) (FIG. 4). This indicated that the LOX-1 gene was properly transcribed.

Since the aforementioned results for the SBOU2 seeds indicated that (1) LOX-1 activity was not detected, (2) only a trace amount of antigen protein reacting with the LOX-1 antibody was present, (3) the presence of a protein with a molecular weight of approximately 57 kD was detected and (4) LOX-1 mRNA was detected, it was concluded that the mechanism for the deficiency of LOX-1 activity in SBOU2 was an aberration after transcription.

Verification Test 4 (Structural Analysis of SBOU2 LOX-1 Gene Intron Regions)

In order to analyze the structure of the intron and exon regions of the LOX-1 gene, genomic DNA of a region comprising all of the exons was isolated. Total DNA from SBOU2 was used as the template. The primers (5'-CACGTCGCCGTCCGATCCATC-3' (SEQ ID NO: 5), 5'-GGTTGCCGATGGCTTAGAT-3' (SEQ ID NO: 4)) were designed based on the reported sequence (DNA Databank: Accession Nos. U83904, L35931). The PCR was carried out with reaction at 94° C., 1 min, 65° C., 2 min and 72° C., 3 min, repeated 31 times, followed by extension reaction at 72° C., 7 min. The obtained DNA fragment was cloned in pCR2.1 (pGLXABAL1) for use as the template for structural analysis. The structural analysis was carried out using an ABI sequencer, and the sequencing reaction was conducted by the dye terminator method. Whole structure is shown in SEQ ID NO: 11 in Sequence Listing.

SEQ ID NO: 1 of the Sequence Listing shows the structure of the region of the reported nucleotide sequence of the LOX-1 gene (WO 02053721) containing the 5th intron. The splicing donor site is the nucleotide sequence 5'-GT-3' at positions 60-61.

The nucleotide sequence of the corresponding region of SBOU2 determined from the analysis results is listed as SEQ ID NO: 2. Clearly in SBOU2, the guanine at position 60 in the splicing donor site is mutated to adenine.

Replacement of the 60th base of SEQ ID NO: 2 with adenine forms a new stop codon (the nucleotide sequence 5'-TGA-3' at positions 58-60 of SEQ ID NO: 2), and therefore presumably translation of the LOX-1 protein ends at that point if the splicing site never changes to the upstream to the 5' end (FIG. 5).

The exon region near the 5th intron is known to be the active center of plant LOX (Shibata and Axelrod (1995), J. Lipid Mediators and Cell Signaling 12:213-228), and it is believed that the aforementioned splicing aberration has a major effect on the LOX-1 enzyme activity.

Verification Test 5 (Analysis of Splicing at 5th Intron)

RT-PCR analysis was conducted in order to confirm that a splicing aberration had actually occurred in the 5th intron.

Figure 6A:
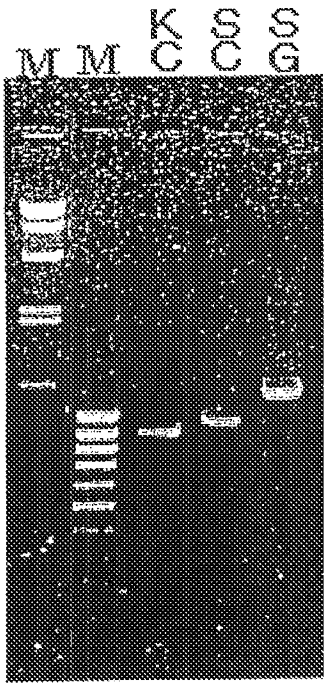
FIGS. 6A and 6B are a pair of electrophoresis images showing the results of analyzing splicing of the LOX-1 mutant gene in Verification Test 5. Image A is an electrophoresis image for amplified fragments containing the 3rd to 5th intron, and B is an electrophoresis image of the same fragments as A after digestion with StuI.

Total RNA was extracted from germinating SBOU2 and Kendall, and a commercially available kit (Roche Diagnostics) was used for synthesis of cDNA to prepare template DNA. PCR was conducted using two different primers (5'-CCATCACGCAGGGCATCCTG-3' (SEQ ID NO: 6), 5'-GCGTTGATGAGCGTCTGCCG-3' (SEQ ID NO: 7)) designed to give an amplified fragment containing the 3rd intron (106 bp), 4th intron (132 bp) and 5th intron (79 bp) in genomic DNA sequence. The PCR was carried out with reaction at 94° C., 1 min, 65° C., 2 min and 72° C., 3 min, repeated 31 times, followed by extension reaction at 72° C., 7 min. Agarose gel electrophoresis of the amplified DNA fragments indicated that the SBOU2 amplified fragment was approximately 80 bp larger than the Kendall amplified fragment (FIG. 6A). An approximately 1.2 Kb fragment was amplified from the SBOU2 genomic DNA, suggesting that the results of the RT-PCR were the results for the expressed RNA.

Figure 6B:
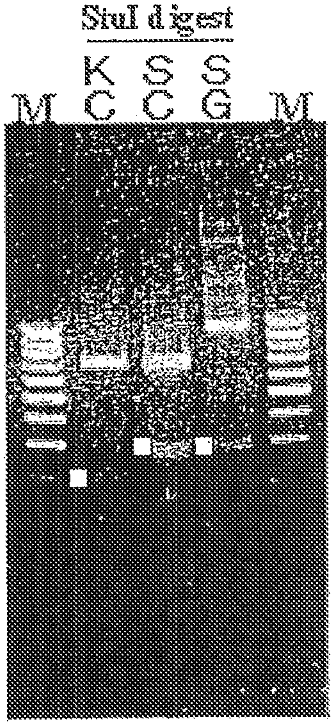

Next, in order to investigate in which of the introns the splicing aberration had occurred (the 3rd intron (106 bp), 4th intron (132 bp) or 5th intron (79 bp)), the amplified fragment was digested at the restriction enzyme StuI site present in the exon region between the 4th intron (132 bp) and 5th intron. As a result, the DNA fragment containing the 5th intron had mobility roughly equivalent to that of one of the amplification fragments from genomic DNA, and therefore an aberration had obviously occurred in splicing of the 5th intron which had either prevented splicing or had shifted the splicing site toward the 3' end (FIG. 6B). That is, clearly, the stop codon newly formed as shown in FIG. 5 had halted translation of the SBOU2 LOX-1 protein at that codon, resulting in loss of LOX-1 activity.

Verification Test 6 (Structural Analysis of LOX-1 cDNA of SBOU2)

In order to elucidate the structure of LOX-1 derived from SBOU2, cDNA was isolated by the same method described above. Amplification was carried out using a primer comprising the BamHI site and start codon (5'-GGATCCATGCTGCTGGGAGGGCTG-3' (SEQ ID NO: 8)) and a primer designed to include the HindIII site and the stop codon (5'-AAGCTTTTAGATGGAGATGCTGTTG-3' (SEQ ID NO: 9). The amplified fragment was cloned in pT7 Blue T-Vector (Novagen) (pBDC1) and then provided for structural analysis. The results of the structural analysis yielded the cDNA nucleotide sequence shown as SEQ ID NO: 10. This cDNA clone clearly includes the entire region of the 5th intron (bases 1554 to 1632 of SEQ ID NO: 10).

Verification Test 7 (Transformation of *E. coli* and Induced Expression)

Figure 7:
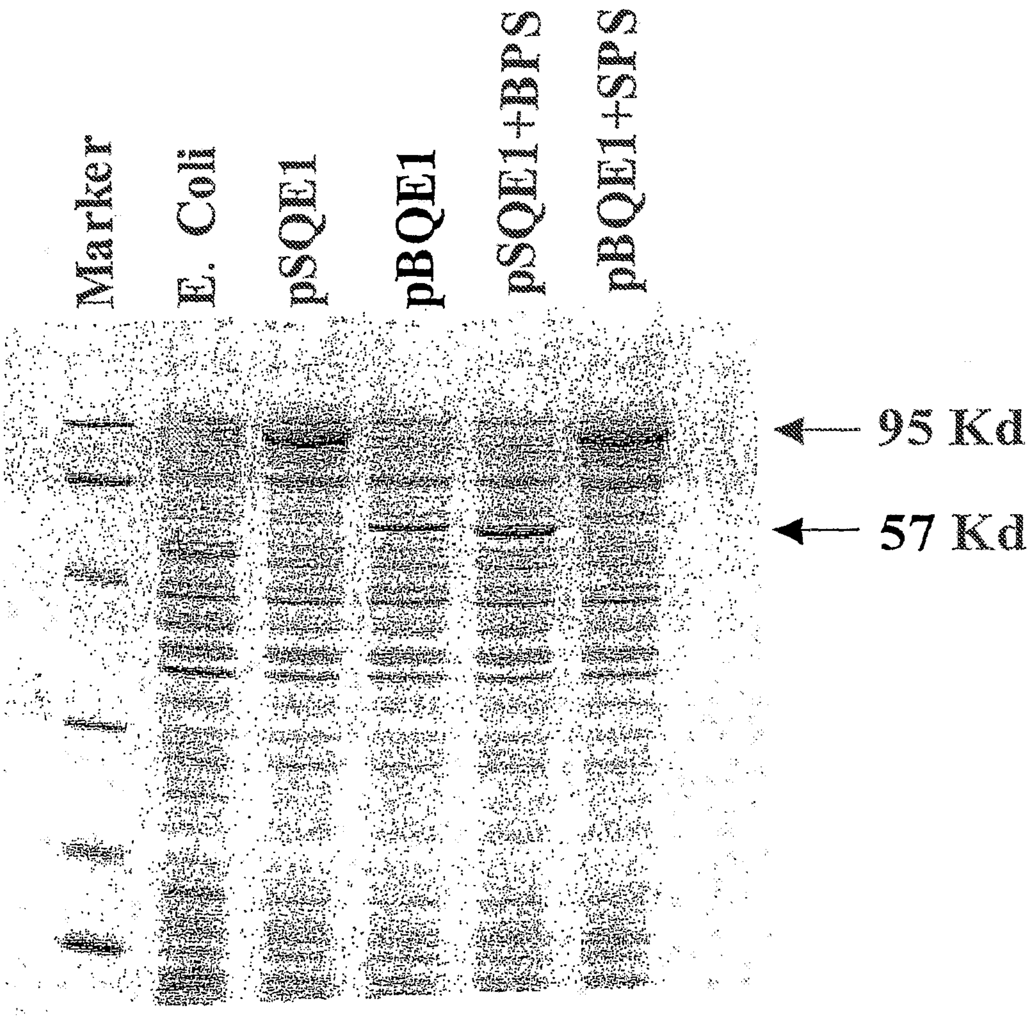
FIG. 7 is an electrophoresis image showing expression-induced proteins in *E. coli* in Verification Test 7 and 8.
Figure 8:
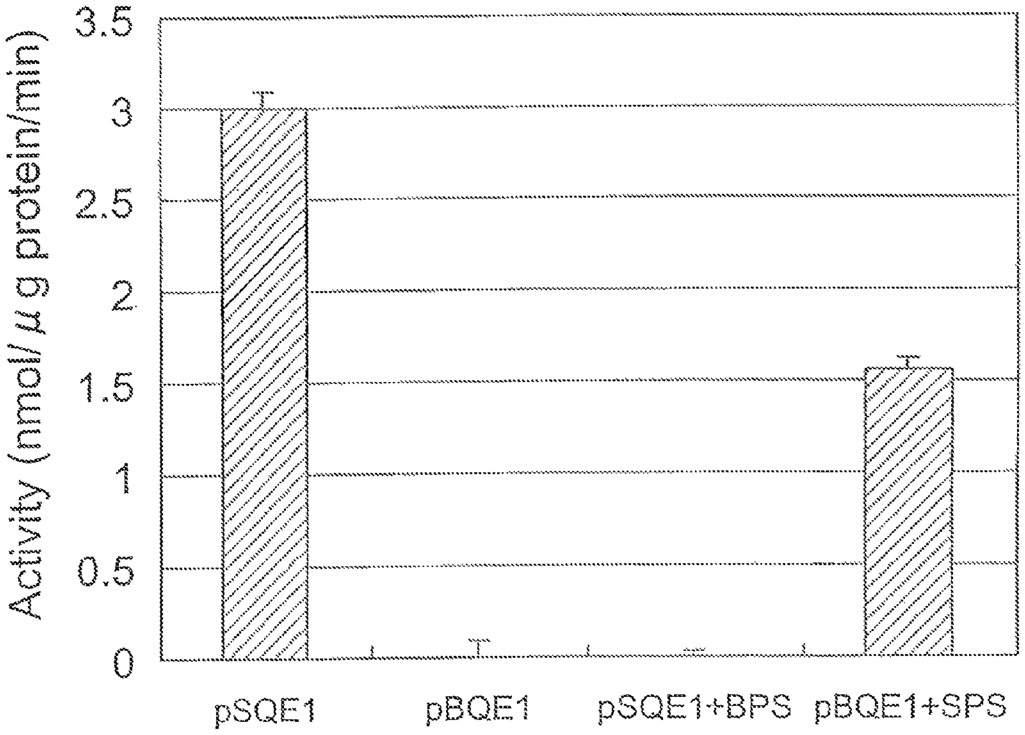
FIG. 8 is a graph showing the activity of LOX-1 expression-induced in *E. coli* in Verification Test 1.

For expression of LOX-1 derived from the Steptoe variety retaining wild type LOX-1, Steptoe-derived cDNA was also isolated in the same manner as above and cloned in *E. coli* (pSDC1), separately from SBOU2. The BamHI-HindIII fragment was cut out from each of the clones pSDC1 and pBDC1 and each of the obtained fragments was inserted at the BamHI-HindIII site of *E. coli* expression vector pQE80L (Qiagen) to obtain *E. coli* expression vectors (pSQE1 (Steptoe cDNA-inserted) and pBQE1 (SBOU2 cDNA-inserted)). These vectors were used to transform *E. coli* JM109, and then expression was induced by IPTG according to the instruction manual by Qiagen. As a result, expression of an approximately 95 kD band was induced with pSQE1/JM109, while expression of an approximately 57 kD band was induced with pBQE1/JM109 (FIG. 7). The *E. coli* cells were disrupted by sonication and the LOX activities of the crude enzyme extracts were assayed. As a result, high LOX activity was found with pSQE1/JM109 while no LOX activity was found with pBQE1/JM109 (FIG. 8). These results perfectly matched the LOX-1 activity and LOX-1 protein analysis results for SBOU2 plants, indicating that the SBOU2 LOX-1 deficiency can be reproduced in *E. coli.*

Verification Test 8 (Exchange Insertion and Expression Test)

Next, a PstI-StuI fragment containing a mutation at the splicing donor site of the 5th intron of pBQE1 (the StuI site is at bases 1502-1507 of SEQ ID NO: 10, and the PstI site is at bases 2048-2053 of SEQ ID NO: 10) was mutually exchanged with the PstI-StuI fragment of the wild type pSQE1 (pSQE1+BPS, pBQE1+SPS), and expression was induced in *E. coli* in the same manner described above. As a result, with pSQE1+BPS/JM109 having the pBQE1-derived PstI-StuI fragment containing a mutation at the splicing donor site of the 5th intron inserted into pSQE1, expression of an approximately 57 kD protein was induced (FIG. 7) and LOX activity was lost (FIG. 8), similar to pBQE1/JM109. Conversely, with pBQE1+SPS/JM109 having the pSQE1-derived PstI-StuI fragment inserted into pBQE1, expression of an approximately 95 kD protein was induced (FIG. 7) and LOX activity was restored (FIG. 8), similar to pSQE1/JM109. The nucleotide sequence of the PstI-StuI fragment of pBQE1 was exactly identical to the wild LOX-1 gene except for the splicing donor site of the 5th intron (G is substituted to A at the 1554th base of SEQ ID NO: 10). These results clearly demonstrated that the presence or absence of the mutation at the splicing donor site of the 5th intron of SBOU2 determines whether LOX-1 activity is present.

Verification Test 9 (Mapping and Selection of Barley Hybrid Variety Using 5th Intron Mutation)

Figure 9:
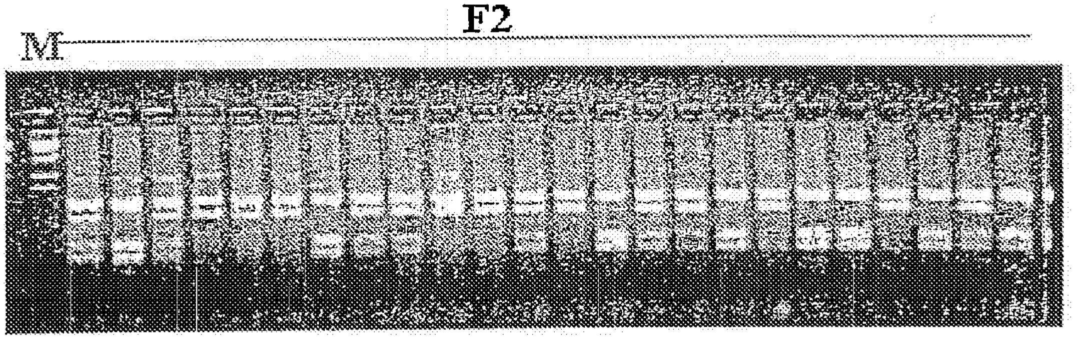
FIG. 9 is an electrophoresis image showing DNA polymorphism in the hybrid 2nd filial generation for Kendall-.times.SBOU2 in Verification Test 9.

In the reported LOX-1 nucleotide sequence, a sequence containing the splicing donor site of the 5th intron (nucleotides 60-63 of SEQ ID NO: 1: 5'-GTAC-3') can be digested by restriction enzyme AfaI (or RsaI) which recognizes the sequence GTAC. The LOX-1 deficient gene was mapped utilizing the fact that a mutation is present in the sequence of this region in the SBOU2 line (nucleotides 60-63 of SEQ ID NO: 2: 5'-ATAC-3') which prevents digestion by AfaI and/or RsaI (FIG. 5). DNA was extracted from the leaves of 144 individuals of a hybrid 2nd filial generation (F2) of a cross between Kendall and SBOU2 line, and PCR was conducted using two different primers (5'-CCATCACGCAGGGCATCCTG 3' (SEQ ID NO: 6), 5'-GCGTTGATGAGCGTCTGCCG-3' (SEQ ID NO: 7)) designed so that the amplified fragment would contain the AfaI site. The PCR was carried out with reaction at 94° C., 1 min, 65° C., 2 min and 72° C., 3 min, repeated 31 times, followed by extension reaction at 72° C., 7 min. Each of the amplified fragments was cleaved with AfaI and analyzed by 2.5% agarose gel electrophoresis (this will hereinafter be referred to as the "AfaI method"). As a result, it was possible to easily distinguish between the SBOU2, Kendall and hetero types (FIG. 9). In addition to the polymorphism examination by the AfaI method, polymorphism in each variety was also examined using a DNA marker (JBC970) near the LOXA gene locus of the barley 4H chromosome bearing the LOX-1 gene (FIG. 10).

A mature seed of each F2 individual was used to examine the LOX activity of the seeds. For lines exhibiting no LOX activity, the activity was measured using several (4-7) seeds (FIG. 10).

As a result of the AfaI method polymorphism examination of the F2 generation and LOX activity measurement of F3 seeds, segregation of the LOX-1 deficient trait of SBOU2 perfectly matched segregation of the AfaI method polymorphism. Thus, this series of genetic analyses clearly showed that the LOX-1 deficient gene of SBOU2 is at the LOXA gene locus.

The results also demonstrated that using the AfaI method as an example of a barley selection method utilizing DNA mutation allows selection of LOX-1 deficient progeny lines at the early stage of the growth, eliminating the need to wait until the seeds have matured.

Example 1

AfaI Polymorphism Examination of Other Barley Varieties

Figure 11:
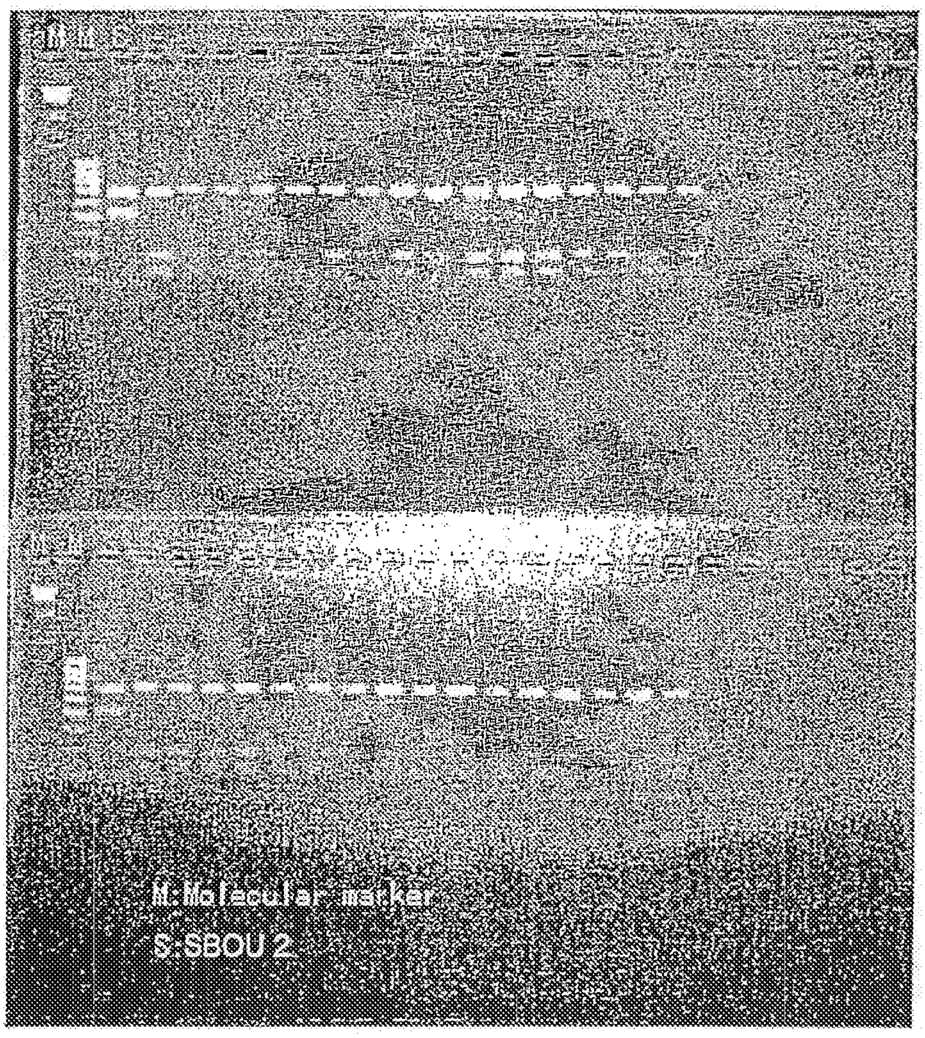
FIG. 11 is an electrophoresis image showing the results of analyzing a general barley variety/line by the AfaI method in Example 1.

General barley varieties/lines were used for AfaI polymorphism examination. A total of 32 varieties/lines were used: Mikamo Golden, Golden Melon, Haruna Nijo, Myogi Nijo, Sakitama Nijo, Wasedori Nijo, Agurimochi, Harupin Nijo, Ryofu, Hokuiku 33, Hokuiku 35, Prior, Schooner, Sloop, Lofty Nijo, Franklin, Betzes, Harrington, Manley, B1251, CDC Kendall, CDC Stratus, CDC Copeland, Hanna, Merit, AC Metcalfe, TR145, Chariot, Stirling, Proctor, Koral and Heartland. As a result of AfaI method polymorphism examination, it was determined that the tested varieties were not the SBOU2 type, but instead were digested at the restriction enzyme AfaI site containing the splicing donor site of the 5th intron (nucleotides 60-63 of SEQ ID NO: 1: 5'-GTAC-3') (FIG. 11). This indicated that these viable lines did not possess a DNA mutation at the AfaI site (nucleotides 60-63 of SEQ ID NO: 1: 5'-GTAC-3'), and therefore that the AfaI method can be effectively utilized for selection of LOX-1 deficient genes among progeny lines.

Example 2

Gene Resource Search

Figure 12:
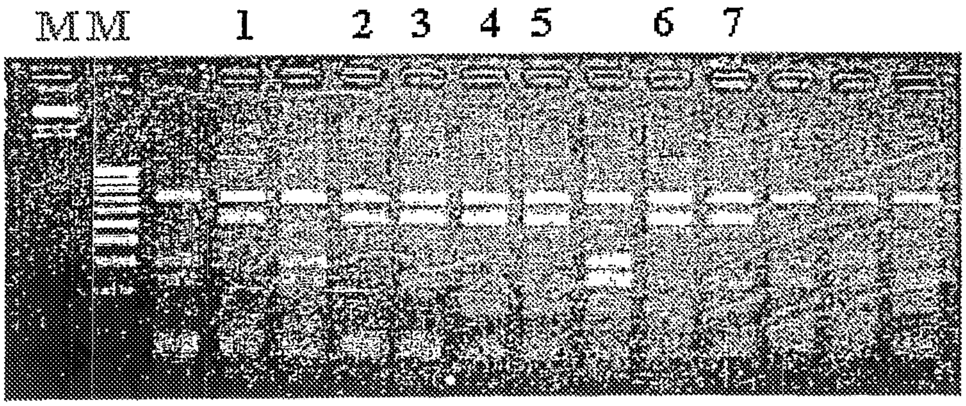
FIG. 12 is an electrophoresis image showing the results of analyzing LOX-1 deficient barley by the AfaI method in Example 2.

Worldwide gene resources of barley (landrace) stocked at Okayama University were examined by the AfaI method. As a result, five new lines (SBOU1, SBOU3, SBOU4, SBOU5 and SBOU6 stocked at Okayama University) were discovered which were not digested at the restriction enzyme AfaI site containing the splicing donor site of the 5th intron (nucleotides 60-63 of SEQ ID NO: 1: 5'-GTAC-3') (FIG. 12).

Figure 13A:
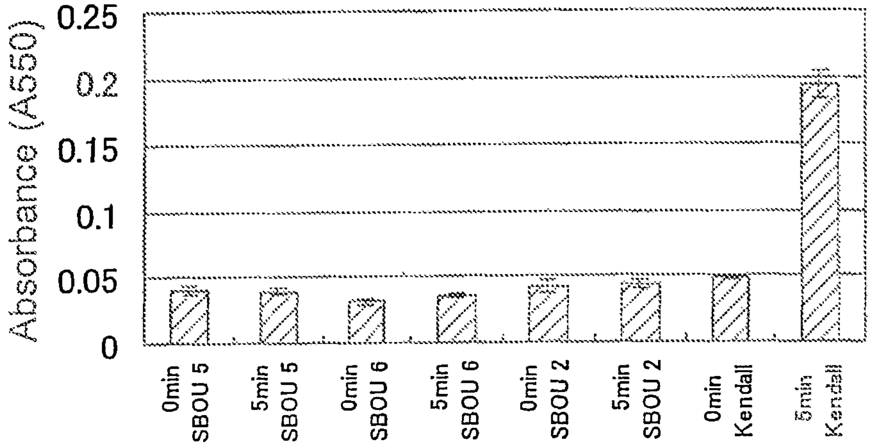
FIGS. 13A and 13B are a pair of graphs showing the results for LOX activity of LOX-1 deficient barley seeds in Example 2. Graph A shows the results at an enzyme reaction time of 5 minutes, and graph B shows the results at an enzyme reaction time of 90 minutes.
Figure 13B:
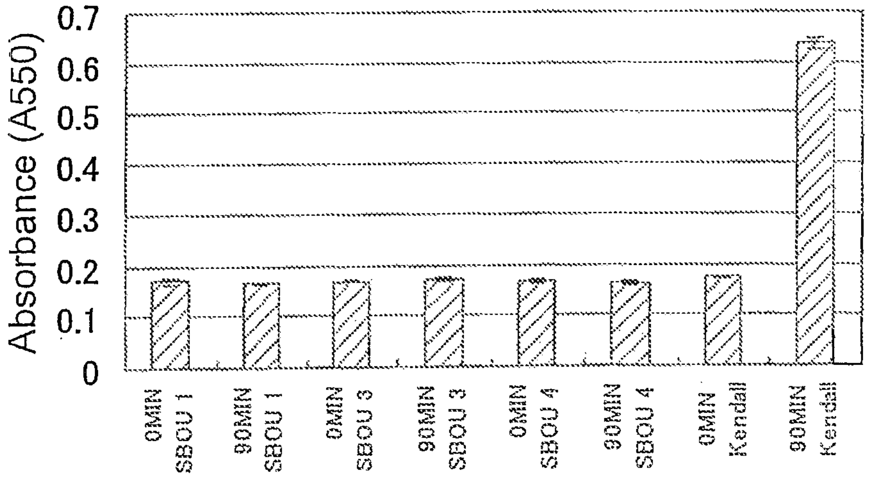

The LOX-1 activity of seeds of these lines was measured by the method described in Search Test 1. The activity measurement for SBOU5 and SBOU6 was carried out by reaction for 5 minutes (FIG. 13A), while activity measurement for SBOU1, SBOU3 and SBOU4 was with an extended reaction time of 90 minutes for clear identification of activity (FIG. 13B). As a result, no significant activity was found in any of the lines (FIGS. 13A and 13B).

This clearly demonstrated that SBOU2 as well as SBOU1, SBOU3, SBOU4, SBOU5 and SBOU6 (SBOU2 type LOX-1 deficient barley) were LOX-1 deficient barley lines. Since all of the lines are landraces and not artificially mutagenized lines, they represent spontaneous mutants for the LOX-1 gene.

The results described above demonstrated that the AfaI method, as an example of a barley selection method utilizing DNA mutation, is a technique allowing not only selection of LOX-1 deficient barley progeny lines, but also efficient selection of LOX-1 deficient barley from barley gene resources.

Example 3

Growth of Barley for Test Brewing

A barley variety, Taishomugi, was crossed with SBOU2, and the obtained first filial generation (F1) was self-pollinated to obtain an F2 generation. The LOX-1 deficient trait was confirmed by the LOX-1 enzyme activity measuring method described in Search test 1 and the AfaI method described in Verification test 9 above, and the group of LOX-1 deficient lines and the group of LOX-1 retaining lines were provided as populations for the seed propagation described below.

Seed propagation was carried out for each line copulation) using a uniform plot or greenhouse until F4 seeds were obtained. When the LOX-1 enzyme activity of the F4 seeds was assayed, it was found that the respective LOX-1 activity traits of the F2 individuals were maintained, indicating that the LOX-1 deficient trait is stably passed on to progeny.

The F4 seeds were used for the following malt production test and malt alcoholic beverage production test.

Example 4

Production of Malt for Test Brewing

A LOX-1 deficient barley F4 population (LOX-F4) comprising barley seeds having no LOX-1 activity and a LOX activity-retaining barley F4 population (LOX+F4) from barley seeds with LOX-1, both derived from the Taishomugi.times.SBOU2 cross, were prepared and used for malting.

The malting was carried out using an Automatic Micromalting System (Phoenix Systems) under conditions with a steeping temperature of 16° C. for a total of 82 hours (5 hr WET/7 hr DRY cycle), germination at 15° C. for 139 hours, and kiln-drying for 29 hours (55° C. for 13.5 hrs, 65° C. for 8 hrs, 75° C. for 3.5 hrs, 83° C. for 4 hrs).

Example 5

Analysis of Malt and Congress Wort

The malt was analyzed according to the EBC Standard Method (European Brewery Convention ed., Analytica EBC (4th Ed), 1987). As a result, no significant difference in analysis values of malt was found between the malts using LOX-F4 and LOX+F4, demonstrating that they can be used for brewing of malt alcoholic beverages for the purpose of comparing the presence or absence of LOX-1 activity (FIG. 14).

Next, 50 g of the malt was used to produce wort by the Congress Method (European Brewery Convention ed., Analytica EBC (4th Ed), 1987), and the lipid oxidation in the congress wort was analyzed.

First, the amount of trans-2-nonenal in the congress wort was measured by the following method. An 8 mL wort sample was placed in a vial, 3 g of NaCl was added, and the vial was capped. Next, a polydimethylsiloxane SPME fiber (Supelco, Inc.) was inserted into the head space of the vial and the vial was incubated at 40° C. for 15 minutes.

The fiber was then inserted into a injection port of a gas chromatography/mass spectrometry equipped with a J&W DB-1 column as the capillary column (30 m.times.0.25 mm, film thickness: 1 μm). Helium was used as the carrier gas (1 mL/min) and oven conditions was from 60° C. to 225° C. (5° C./min), in select ion mode (m/z: 70). The quantitation was performed by the standard addition method using trans-2-nonenal (Sigma) as standard sample.

As a result, the trans-2-nonenal concentrations of the congress worts produced using LOX-F4 and LOX+F4 were 0.36 ppb and 3.85 ppb, respectively. Thus, it was demonstrated that production of wort using malt according to the present invention allows production of trans-2-nonenal to be inhibited by as much as 1/10 or less of conventional malt.

The nonenal potential of the congress wort was measured by the following method. First, the congress wort was boiled for 2 hours by the method of Drost et al. (Drost, B. W., van den Berg, R., Freijee, F. J. M., van der Velde, E. G., and Hollemans, M., J. Am. Soc. Brew. Chem., 48, 124-131, 1990). The amount of trans-2-nonenal in the sample was then measured by the trans-2-nonenal measuring method described above, and the nonenal potential of the congress wort was calculated.

As a result, the nonenal potentials of the congress worts produced using LOX-F4 and LOX+F4 were 2.74 ppb and 11.9 ppb, respectively. Since the nonenal potential is known as an index of product aging (Drost, B. W., et al., J. Am. Soc. Brew. Chem., 48, 124-131, 1990; Ueda et al. (2001) EBC-proceedings 55:p 3 28th Congress), malt produced from barley according to the invention can be utilized for brewing of malt alcoholic beverages to significantly improve flavor stability of malt alcoholic beverages.

Figure 15:
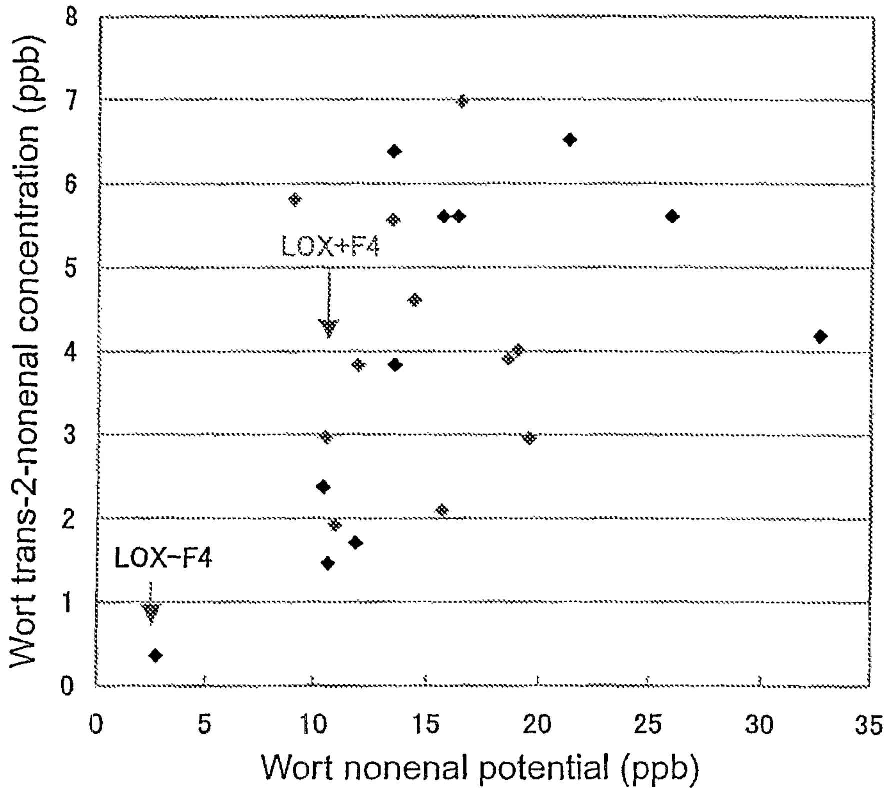
FIG. 15 is a dot graph showing trans-2-nonenal concentrations and nonenal potentials for wort in Example 5.

The trans-2-nonenal concentrations and nonenal potentials of the congress worts produced using LOX-F4 are shown in FIG. 15 in comparison with those of congress worts produced using commercially available malt. As is clear by the results shown in FIG. 15, the worts of the present invention exhibited values that have not been achievable with conventional barley.

These results demonstrated that utilizing barley according to the present invention allows production of malt with a superior level of quality not exhibited by conventional products.

The THOD concentrations of the congress worts were measured by high performance liquid chromatography-mass spectrometry (HPLC-MS) analysis. The HPLC conditions were as follows. The flow rate of the mobile phase was 0.3 mL/min, using a mixed solution of 0.5% acetic acid (Solution A) and acetonitrile (Solution B) as the mobile phase, with a linear gradient of Solution A: Solution B=35: 65 (0 min) to Solution A: Solution B=5: 95 (30 min). The column used was a Waters Asymmetry column (No. 106005; C18, 3.5 μm: 2.1×150 mm), the column temperature was 50° C., and a Model 1100 HPLC system (Hewlett-Packard) was used for separation of 5 μL, sample of wort or malt alcoholic beverages. Mass analysis was performed using a Waters ZQ, with monitoring of mass 329 under ES ionization negative mode. The THOD standard solution used was a beer extract sample (Kobayashi, N., et al., J. Biosci. Bioeng., 90, 69-73, 2000).

As a result, the THOD concentrations of the congress worts produced using LOX-F4 and LOX+F4 were 6.5 ppm and 14.7 ppm, respectively, thus demonstrating that production of wort using malt according to the present invention can inhibit the wort THOD concentration to ½ or below.

As mentioned above, THOD is produced by conversion from linoleic acid by the action of malt LOX-1 and malt peroxygenase activity in the mashing step, but since malt peroxygenase activity is thought to be the rate-limiting step for THOD production (Kuroda, H., et al., J. Biosci. Bioeng., 93, 73-77, 2002), it has not been clear to what degree reduced malt LOX-1 activity inhibits production of THOD. However, the results in the examples provided in the present specification have demonstrated that using malt produced from barley seeds with no LOX-1 activity reduces THOD concentration in wort. Since THOD survives to the final product without being metabolized by yeast (Kobayashi, N., et al., J. Inst. Brew., 106, 107-110 (2000)), the use of malt derived from barley according to the present invention can clearly result in production of malt alcoholic beverages with good flavor quality and foam quality.

Example 6

Test Brewing of Malt Alcoholic Beverages

1. Production and Analysis of Wort

The LOX-F4 malt and LOX+F4 malt obtained in Example 4 above were mashed with a 50 L scale mashing apparatus according to the standard mashing methods for Happoshu, low malt alcoholic beverage (malt content: 24%). The mashing conditions were as follows.

1.5 kg of each malt was mashed alone with 15 L of mashing water according to a diagram of 50° C. for 20 min, 65° C. for 30 min and 75° C. for 3 min. After mashing, wort lautering was carried out with a lauter tun. 35 L of lautered worts were obtained.

Before boiling, the lautered wort was mixed with 5 kg of starch syrup (75% saccharides). 13 g of hop pellets (bitterness unit: 87.0 BU (EBC)) was added into the wort. After boiling for 70 minutes, the boiled wort was cooled to 10° C. The extract content of cooled worts were adjusted by water addition to 11.6-11.8%.

The obtained worts were analyzed according to the EBC Standard Method (European Brewery Convention ed., Analytica EBC (4th Ed), 1987). The analysis values are shown in Table 1. As seen in Table 1, no distinct difference was found between LOX-F4 and LOX+F4 with regard to parameters.

TABLE 1

| Variety | LOX + F4 | LOX − F4 |
|---|---|---|
| Specific gravity | 1.0475 | 1.0467 |
| Extract (%) | 11.78 | 11.60 |
| Real nonfermented extract (%) | 3.45 | 3.38 |
| Real attenuation (%) | 70.7 | 70.9 |
| Apparent nonfermented extract (%) | 1.54 | 1.52 |
| Apparent attenuation limit(%) | 86.9 | 86.9 |
| pH | 5.88 | 5.93 |
| Color (° EBC) | 2.1 | 2.1 |
| BU | 31.2 | 27.3 |
| Total nitrogen (mg/100 ml) | 24 | 22 |
| Polyphenol (mg/L) | 44 | 48 |
| FAN (mg/L) | 46 | 51 |

2. Production of Malt Alcoholic Beverage (Happoshu, Low Malt Alcoholic Beverage)

The wort obtained in 1. above was transferred to a steam-sterilized 30 L scale cylindroconical tank, and then yeast was added to an initial concentration of 30 million cells/ml for main fermentation at 13° C. When the extract content in the fermentation liquid fell to 2.5%, it was transferred to a new similar tank for a storage step. The storage step was carried out at 13° C. for the first 6 days and then at 0° C. for 2 weeks thereafter.

After finishing the storage step, fermentation liquid was supplied to a beer filtration and filling apparatus. The malt alcoholic beverage was filtered and filled into bottles.

3. Analysis of Malt Alcoholic Beverage

The malt alcoholic beverage obtained in 2. above was analyzed as follows.

Analysis according to the EBC Standard Method shows that no significant difference was found between LOX-F4 and LOX+F4 in terms of the general analysis parameters other than the lipid oxidation parameters (Table 2).

TABLE 2

| Variety | LOX + F4 | LOX − F4 |
|---|---|---|
| Specific gravity | 1.00562 | 1.00565 |
| Original wort extract (%) | 11.82 | 11.56 |
| Real extract (%) | 3.43 | 3.38 |
| Real attenuation (%) | 71.0 | 70.7 |
| Apparent extract (%) | 1.44 | 1.45 |
| Apparent attenuation (%) | 87.8 | 87.4 |
| Alcohol (vol %) | 5.5 | 5.35 |
| Alcohol (w/w %) | 4.33 | 4.21 |
| pH | 3.51 | 3.28 |
| Gas pressure (20° C.) kg/cm | 2.35 | 2.55 |
| Color (° EBC) | 1.5 | 1.7 |
| Total nitrogen (mg/100 ml) | 16 | 19 |
| BU | 11.6 | 9.5 |
| Polyphenol (mg/L) | 45 | 43 |
| FAN (mg/L) | 10 | 12 |

The foam stability of the malt alcoholic beverage obtained in 2. above was analyzed by the following method.

The foam stability analysis was conducted by the NIBEM method. Upon analysis of the foam stability using a Haffmans Foam Stability Tester (Table 3), the LOX-F4 barley clearly had higher foam stability, with a NIBEM value of 21 points higher than the LOX+F4 barley.

Also, as a result of measuring the THOD concentration by the method described in Example 5 above, the THOD content of LOX-F4 exhibited a reduction to less than half of that of LOX+F4 (Table 3).

These results clearly demonstrated that the malt alcoholic beverage production method of the invention enable to produce the malt alcoholic beverage with reduced THOD content and improved foam retention.

TABLE 3

| Variety | LOX + F4 | LOX − F4 |
|---|---|---|
| NIBEM | 239 | 260 |
| THOD (mg/L) | 3.6 | 1.7 |

The malt alcoholic beverage obtained in 2. above was then subjected to the following sensory test by 13 panelists for comparison of the flavor stability.

First, the LOX-F4 and LOX+F4 malt alcoholic beverages were stored at 37° C. for one week. They were then poured into cups at ordinary drinking temperature and provided for sensory test by panelists for evaluation of the off-flavor and total staleness on a scale of 0-4 (with a higher value representing progressive aging) (Tables 4A, B).

As a result, 10 of the 13 panelists assigned lower scores to LOX-F4 for off-flavor, and therefore LOX-F4 exhibited a lower score (average) than LOX+F4. The difference according to a paired t test was determined to be significant at the 5% probability (Table 4A).

For the total staleness, 11 of the 13 panelists assigned lower scores to LOX-F4, and therefore LOX-F4 exhibited a lower score (average) than LOX+F4. The difference according to a paired t test was determined to be significant at the 5% probability level (Table 4B).

The above sensory test and statistical analysis demonstrated that LOX-F4 had lower off-flavor and total staleness than LOX+F4.

TABLE 4A

| Off-flavor | LOX + F4 | LOX − F4 |
|---|---|---|
| Panelist 1 | 3 | 2 |
| Panelist 2 | 1 | 2 |
| Panelist 3 | 3 | 2 |
| Panelist 4 | 2.5 | 2.5 |
| Panelist 5 | 2 | 2 |
| Panelist 6 | 2.5 | 2 |
| Panelist 7 | 2.5 | 1.5 |
| Panelist 8 | 2.5 | 1 |
| Panelist 9 | 1 | 0.5 |
| Panelist 10 | 2.5 | 2 |
| Panelist 11 | 2 | 1.5 |
| Panelist 12 | 2.5 | 2 |
| Panelist 13 | 2 | 1.5 |
| Average | 2.2 | 1.7 |

TABLE 4B

| Total staleness | LOX + F4 | LOX − F4 |
|---|---|---|
| Panelist 1 | 2.5 | 2 |
| Panelist 2 | 1 | 2 |
| Panelist 3 | 3 | 2 |
| Panelist 4 | 3 | 2.5 |
| Panelist 5 | 2.5 | 2 |
| Panelist 6 | 2.5 | 2 |
| Panelist 7 | 2.5 | 1.5 |
| Panelist 8 | 2.5 | 1.5 |
| Panelist 9 | 1 | 0.5 |
| Panelist 10 | 2.5 | 2 |
| Panelist 11 | 2 | 1.5 |
| Panelist 12 | 2.5 | 2.5 |
| Panelist 13 | 2 | 1.5 |
| Average | 2.3 | 1.8 |

As a result of measuring the trans-2-nonenal content of the malt alcoholic beverage obtained in 2 above, LOX-F4 had a lower trans-2-nonenal content than LOX+F4 before and after storage at 37° C. for one week. The trans-2-nonenal content of LOX-F4 was reduced to approximately ⅓ compared to that of LOX+F4 after storage (Table 5).

TABLE 5

| trans-2-nonenal conc. | LOX + F4 | LOX − F4 |
|---|---|---|
| Before storage | 0.02 | 0.01 |
| After storage | 0.35 | 0.12 |

(Unit: ppb)

These results of the sensory test and results of analysis of the trans-2-nonenal content in the malt alcoholic beverages demonstrated that the malt alcoholic beverage production method of the invention enable to produce the malt alcoholic beverages with improved flavor stability.

Finally, the body and smoothness of the malt alcoholic beverage obtained in 2. above were analyzed by sensory test and with a lipid membrane sensor.

First, an sensory test was carried out by 13 well-trained panelists for comparison of the flavor quality. LOX-F4 and LOX+F4 malt alcoholic beverages were provided for sensory test, and the body and smoothness were evaluated on a scale of 0-4 (with higher scores for fuller body and better smoothness) (Table 6).

For body, no significant difference (5% probability level) was found between LOX-F4 and LOX+F4 (Table 6A).

For smoothness, 8 of 13 panelists assigned higher scores to LOX-F4 (Table 6B). LOX-F4 had a higher (average) score than LOX+F4, and the difference according to a paired t test was determined to be significant at the 5% probability level.

These results demonstrated that brewing of malt alcoholic beverages using LOX-F4 can improve smoothness without affecting body.

TABLE 6A

| Body | LOX + F4 | LOX − F4 |
|---|---|---|
| Panelist 1 | 2 | 1 |
| Panelist 2 | 3 | 2 |
| Panelist 3 | 3 | 2.5 |
| Panelist 4 | 3.5 | 3.5 |
| Panelist 5 | 3 | 3 |
| Panelist 6 | 2 | 2 |
| Panelist 7 | 2 | 2 |
| Panelist 8 | 3 | 2 |
| Panelist 9 | 3 | 2 |
| Panelist 10 | 2.5 | 2.5 |
| Panelist 11 | 3 | 2 |
| Panelist 12 | 2 | 3 |
| Panelist 13 | 2 | 3 |
| Average | 2.6 | 2.3 |

TABLE 6B

| Smoothness | LOX + F4 | LOX − F4 |
|---|---|---|
| Panelist 1 | 1 | 2 |
| Panelist 2 | 1 | 3 |
| Panelist 3 | 1.5 | 3 |
| Panelist 4 | 3 | 3 |
| Panelist 5 | 1 | 1 |
| Panelist 6 | 2 | 2 |
| Panelist 7 | 2 | 3 |
| Panelist 8 | 1.5 | 3 |
| Panelist 9 | 1 | 2 |
| Panelist 10 | 1.5 | 2 |
| Panelist 11 | 2 | 3 |
| Panelist 12 | 3 | 2 |
| Panelist 13 | 3 | 2 |
| Average | 1.8 | 2.4 |

The body and smoothness were also evaluated using a lipid membrane sensor, according to the method of Kaneda et al. (Kaneda, H. et al., J. Biosci. Bioeng., 92, 221-226, 2001) (Table 7).

The body was evaluated based on adsorption onto the lipid membrane, and the results showed no statistically significant difference (5% probability level) between adsorption with LOX-F4 and LOX+F4 (Table 7A).

The smoothness was evaluated based on the duration of adsorption onto the lipid membrane (with a higher duration of adsorption indicating poorer smoothness), and LOX-F4 exhibited a residue of approximately ¼ compared to LOX+F4, with a significant difference at a probability level of 1% (Table 7B).

TABLE 7A

| Body | Adsorption | S.D. |
|---|---|---|
| LOX + F4 | 189 | 4 |
| LOX − F4 | 187 | 3 |

(Unit: Hz)

(No significant difference at 5% probability level)

TABLE 7B

| Smoothness | Residue | S.D. |
|---|---|---|
| LOX + F4 | 12 | 3 |
| LOX − F4 | 3 | 3 |

(Unit: Hz)

(Significant Difference at 1% Probability Level)

No correlation has been hitherto found between barley LOX-1 activity and THOD production levels in mashing steps (Kobayashi, N. et al., (2000) J. Biosci. Bioeng. 90:69-73), and it has been unclear to what extent THOD production is reduced by inhibition of barley LOX-1. Moreover, it has not been possible in the prior art to predict whether smoothness can be enhanced as a result of such inhibition of barley LOX-1. However, the results of the sensory test and analysis of product body and smoothness using a lipid membrane sensor in the examples described in the present specification has demonstrated for the first time that barley containing the gene claimed herein can be utilized to enhance product smoothness without affecting product body.

Example 7

Test Brewing of Malt Alcoholic Beverages Using Processed Barley

1. Production and Analysis of Wort

Using processed barley of LOX-F5 and LOX+F5, the next generations of the lines obtained in Example 3 above, as the adjunct mashing was carried out with a 50 L scale mashing apparatus according to the standard mashing methods for Happoshu, low malt alcoholic beverage (malt content: 24%, processed barley content: 76%). The mashing conditions were as follows.

1.2 kg of a commercially available malt for the brew and 3.8 kg of each processed barley was mashed with 20 L of mashing water according to a diagram of 50° C. for 30 min, 65° C. for 60 min and 75° C. for 3 min (enzymes such as α-amylase and β-glucanase were added because of the high content of the processed barley). After mashing, wort lautering was carried out with a lauter tun. 40 L of lautered worts were obtained.

53 g of hop pellets (bitterness unit: 25.6 BU (EBC)) was added into the obtained lautered worts. After boiling for 80 minutes, the boiled wort was cooled to 10° C. The extract content of cooled worts were adjusted by water addition to 7.5-7.6%.

The obtained worts were analyzed according to the EBC Standard Method. The analysis values are shown in Table 8. As seen in Table 8, no distinct difference was found between LOX-F5 and LOX+F5 with regard to parameters.

TABLE 8

| Variety | LOX + F5 | LOX − F5 |
|---|---|---|
| Specific gravity | 1.0303 | 1.0296 |
| Extract (%) | 7.63 | 7.46 |
| Real nonfermented extract (%) | 2.00 | 2.06 |
| Real attenuation (%) | 73.8 | 72.4 |
| Apparent nonfermented extract (%) | 0.67 | 0.71 |
| Apparent attenuation limit(%) | 91.2 | 90.5 |
| pH | 5.69 | 5.71 |
| Color (°EBC) | 5.7 | 6.5 |
| BU | 31.7 | 30.9 |
| Total nitrogen (mg/100 ml) | 45 | 47 |
| Polyphenol (mg/L) | 159 | 137 |
| FAN (mg/L) | 72 | 72 |

2. Production of Malt Alcoholic Beverage (Happoshu, Low Malt Alcoholic Beverage

The wort obtained in 1. above was transferred to a steam-sterilized 30 L scale cylindroconical tank, and then yeast was added to an initial concentration of 30 million cells/ml for main fermentation at 15° C. When the extract content in the fermentation liquid fell to 1.3%, it was transferred to a new similar tank for a storage step. The storage step was carried out at 13° C. for the first 5 days and then at 0° C. for 2 weeks thereafter.

After finishing the storage step, fermentation liquid was supplied to a beer filtration and filling apparatus. The malt alcoholic beverage was filtered and filled into bottles.

3. Analysis of Malt Alcoholic Beverage

The malt alcoholic beverage obtained in 2 above was analyzed as follows.

Analysis according to the EBC Standard Method shows that no significant difference was found between LOX-F5 and LOX+F5 in terms of the general analysis parameters other than the lipid oxidation parameters (Table 9).

TABLE 9

| Variety | LOX + F5 | LOX − F5 |
|---|---|---|
| Specific gravity | 1.00307 | 1.00338 |
| Original wort extract (%) | 7.77 | 7.60 |
| Real extract (%) | 2.11 | 2.14 |
| Real attenuation (%) | 73.7 | 72.7 |
| Apparent extract (%) | 0.79 | 0.87 |
| Apparent attenuation (%) | 89.9 | 88.6 |
| Alcohol (vol %) | 3.62 | 3.49 |
| Alcohol (w/w %) | 2.86 | 2.75 |
| pH | 4.58 | 4.59 |
| Gas pressure (20° C.) kg/cm | 2.29 | 2.38 |
| Color (°EBC) | 4.0 | 4.2 |
| Total nitrogen (mg/100 ml) | 28 | 27 |
| BU | 16.8 | 15.3 |
| Polyphenol (mg/L) | 111 | 91 |
| FAN (mg/L) | 16 | 16 |

The foam stability of the malt alcoholic beverage obtained in 2 above was analyzed by the following method.

The foam stability analysis was conducted by the NIBEM method. Upon analysis of the foam stability using a Haffmans Foam Stability Tester (Table 10), the LOX-F5 barley clearly had higher foam stability, with a NIBEM value of 17 points higher than the LOX+F5 barley.

Also, as a result of measuring the THOD concentration by the method described in Example 5 above, the THOD content in the malt alcoholic beverage of LOX-F5 exhibited a reduction to less than half of that of LOX+F5.

These results clearly demonstrated that the malt alcoholic beverage production method of the invention enable to produce the malt alcoholic beverage with reduced THOD content and improved foam retention.

TABLE 10

| Variety | LOX + F5 | LOX − F5 |
|---|---|---|
| NIBEM | 279 | 296 |
| THOD (peak area ratio) | 728 | 237 |

The values of THOD indicate the relative values, where the peak areas of the internal standard are 100.

The malt alcoholic beverage obtained in 2 above was then subjected to the following sensory test by 13 panelists for comparison of the flavor stability. The specific method of the sensory test is the same as that described in Example 6.

As a result, 11 of the 13 panelists assigned lower scores to LOX-F5 for off-flavor, and therefore LOX-F5 exhibited a lower score (average) than LOX+F5. The difference according to a paired t test was determined to be significant at the 5% probability (Table 11A).

For the total staleness, 12 of the 13 panelists assigned lower scores to LOX-F5, and therefore LOX-F5 exhibited a lower score (average) than LOX+F5. The difference according to a paired t test was determined to be significant at the 5% probability level (Table 11B).

The above sensory test and statistical analysis demonstrated that LOX-F5 had lower off-flavor and total staleness than LOX+F5.

TABLE 11A

| Off-flavor | LOX + F5 | LOX − F5 |
|---|---|---|
| Panelist 1 | 2 | 1.5 |
| Panelist 2 | 3 | 2 |
| Panelist 3 | 3 | 2 |
| Panelist 4 | 2 | 1.5 |
| Panelist 5 | 3 | 2 |
| Panelist 6 | 2 | 1 |
| Panelist 7 | 2.5 | 3 |
| Panelist 8 | 2 | 1 |
| Panelist 9 | 2.5 | 2 |
| Panelist 10 | 2 | 1 |
| Panelist 11 | 3 | 2 |
| Panelist 12 | 2.5 | 1.5 |
| Panelist 13 | 2 | 3 |
| Average | 2.4 | 1.8 |

TABLE 11B

| Total staleness | LOX + F5 | LOX − F5 |
|---|---|---|
| Panelist 1 | 2 | 1.5 |
| Panelist 2 | 3 | 1 |
| Panelist 3 | 3.5 | 1.5 |
| Panelist 4 | 2 | 1.5 |
| Panelist 5 | 3 | 2 |
| Panelist 6 | 2 | 1 |
| Panelist 7 | 2.5 | 3 |
| Panelist 8 | 2 | 1 |
| Panelist 9 | 3 | 2 |
| Panelist 10 | 2 | 1 |
| Panelist 11 | 3 | 2 |
| Panelist 12 | 2.5 | 1.5 |
| Panelist 13 | 3 | 1.5 |
| Average | 2.6 | 1.6 |

As a result of measuring the trans-2-nonenal content of the malt alcoholic beverage obtained in 2 above before and after storage at 37° C. for one week, LOX-F5 had a similar trans-2-nonenal content as LOX+F5 before the storage. The trans-2-nonenal content of LOX-F5 was reduced to approximately ½ compared to that of LOX+F5 after the storage (Table 12).

TABLE 12

| trans-2-nonenal conc. | LOX + F5 | LOX − F5 |
|---|---|---|
| Before storage | 0.06 | 0.06 |
| After storage | 0.16 | 0.09 |

(Unit: ppb)

Example 8

Test Brewing of Malt Alcoholic Beverages

1. Production and Analysis of Wort

The LOX-F4 malt and LOX+F4 malt obtained by the same method as that described in Example 4 above were mashed with a 50 L scale mashing apparatus according to the standard mashing methods for beer (malt content: 71%). The mashing conditions were as follows.

5.0 kg of the test malt above and 2.0 kg of adjunct (corn starch, corn grits and broken rice) were mashed with 23 L of mashing water according to a diagram of 50° C. for 20 min, 65° C. for 40 min and 75° C. for 3 min. After mashing, wort lautering was carried out with a lauter tun. 40 L of lautered worts were obtained.

40 g of hop pellets (bitterness unit: 44.9 BU (EBC)) was added into the obtained lautered worts. After boiling for 90 minutes, the boiled wort was cooled to 10° C. The extract content of cooled worts were adjusted by water addition to 10.8-11.1%.

The obtained worts were analyzed according to the EBC Standard Method. The analysis values are shown in Table 13. As seen in Table 13, no distinct difference was found between LOX-F4 and LOX+F4 with regard to parameters.

TABLE 13

| Variety | LOX + F4 | LOX − F4 |
|---|---|---|
| Specific gravity | 1.0444 | 1.0433 |
| Extract (%) | 11.05 | 10.79 |
| Real nonfermented extract (%) | 3.05 | 3.05 |
| Real attenuation (%) | 72.4 | 71.7 |
| Apparent nonfermented extract (%) | 1.25 | 1.31 |
| Apparent attenuation limit(%) | 88.7 | 87.9 |
| pH | 5.71 | 5.68 |
| Color (°EBC) | 6.3 | 6.5 |
| BU | 38.0 | 38.2 |
| Total nitrogen (mg/100 ml) | 77 | 78 |
| Polyphenol (mg/L) | 150 | 147 |
| FAN (mg/L) | 153 | 148 |

2. Production of Malt Alcoholic Beverage (Beer)

The wort obtained in 1 above was transferred to a steam-sterilized 30 L scale cylindroconical tank, and then yeast was added to an initial concentration of 15 million cells/ml for main fermentation at 10.5° C. When the extract content in the fermentation liquid fell to 2.5%, it was transferred to a new similar tank for a storage step. The storage step was carried out at 8° C. for the first 8 days and then at 0° C. for 2 weeks thereafter.

After finishing the storage step, fermentation liquid was supplied to a beer filtration and filling apparatus. The malt alcoholic beverage was filtered and filled into bottles.

3. Analysis of Malt Alcoholic Beverage

The foam stability of the malt alcoholic beverage obtained in 2 above was analyzed by the following method. The foam stability analysis was conducted by the NIBEM method. Upon analysis of the foam stability using a Haffmans Foam Stability Tester (Table 14), the LOX-F4 barley clearly had higher foam stability, with a NIBEM value of 30 points higher than the LOX+F4 barley.

Also, as a result of measuring the THOD concentration by the method described in Example 5 above, the THOD content in the malt alcoholic beverage of LOX-F4 exhibited a reduction to less than half of that of LOX+F4.

These results clearly demonstrated that the malt alcoholic beverage production method of the invention enable to produce the malt alcoholic beverage with reduced THOD content and improved foam retention.

TABLE 14

| Variety | LOX + F4 | LOX − F4 |
|---|---|---|
| NIBEM | 273 | 303 |
| THOD (peak area ratio) | 499 | 221 |

The values of THOD indicate the relative values, where the peak areas of the internal standard are 100.

The malt alcoholic beverage obtained in 2 above was then subjected to the following sensory test by 13 panelists for comparison of the flavor stability. The specific method of the sensory test is the same as that described in Example 6.

As a result, 11 of the 13 panelists assigned lower scores to LOX-F4 for off-flavor, and therefore LOX-F4 exhibited a lower score (average) than LOX+F4. The difference according to a paired t test was determined to be significant at the 5% probability (Table 15A).

For the total staleness, 12 of the 13 panelists assigned lower scores to LOX-F4, and therefore LOX-F4 exhibited a lower score (average) than LOX+F4. The difference according to a paired t test was determined to be significant at the 5% probability level (Table 15B).

The above sensory test and statistical analysis demonstrated that LOX-F4 had lower off-flavor and total staleness than LOX+F4.

TABLE 15A

| Off-flavor | LOX + F4 | LOX − F4 |
|---|---|---|
| Panelist 1 | 2.5 | 2 |
| Panelist 2 | 3 | 3.5 |
| Panelist 3 | 3.5 | 2 |
| Panelist 4 | 2.5 | 2 |
| Panelist 5 | 1.5 | 1 |
| Panelist 6 | 3 | 1 |
| Panelist 7 | 2.5 | 3 |
| Panelist 8 | 3 | 2 |
| Panelist 9 | 2 | 1.5 |
| Panelist 10 | 2 | 1 |
| Panelist 11 | 3 | 1.5 |
| Panelist 12 | 1.5 | 1 |
| Panelist 13 | 2 | 1 |
| Average | 2.5 | 1.7 |

TABLE 15B

| Total staleness | LOX + F4 | LOX − F4 |
|---|---|---|
| Panelist 1 | 3 | 2 |
| Panelist 2 | 3 | 3.5 |
| Panelist 3 | 3 | 1.5 |
| Panelist 4 | 2.5 | 2 |
| Panelist 5 | 1.5 | 1 |
| Panelist 6 | 3 | 1 |
| Panelist 7 | 3 | 2.5 |
| Panelist 8 | 3 | 2 |
| Panelist 9 | 2 | 1 |
| Panelist 10 | 2 | 1 |

TABLE 15B-continued

| Total staleness | LOX + F4 | LOX − F4 |
|---|---|---|
| Panelist 11 | 3 | 1 |
| Panelist 12 | 1.5 | 1 |
| Panelist 13 | 2 | 1 |
| Average | 2.5 | 1.6 |

These results of the sensory test and results of analysis of the trans-2-nonenal content in the malt alcoholic beverages demonstrated that the malt alcoholic beverage production method of the invention enable to produce the malt alcoholic beverages with improved flavor stability.

INDUSTRIAL APPLICABILITY

It is possible to provide a LOX-1 mutant gene which is useful for production of malt alcoholic beverages exhibiting improved flavor stability and foam stability without gene manipulation, a selection method for LOX-1 deficient barley, materials for malt alcoholic beverages derived from barley obtained by the selection method, and a method for production of malt alcoholic beverages using the materials for malt alcoholic beverages.

The invention claimed is:

1. A malt composition produced from a barley plant or a part thereof comprising a lipoxygenase-1 protein comprising an amino acid sequence encoded by nucleotides 1 to 1554 of SEQ ID NO:10 and wherein the barley plant is deficient in lipoxygenase activity.

2. A wort composition prepared from the malt composition of claim 1.

3. A beverage that is prepared from the malt composition of claim 1.

4. A method of producing a malt composition; a wort composition; a beverage; or a combination thereof; the method comprising processing a barley plant or a part thereof comprising a lipoxygenase-1 protein comprising an amino acid sequence encoded by nucleotides 1 to 1554 of SEQ ID NO:10 and wherein the barley plant is deficient in lipoxygenase activity into a malt composition, a wort composition, a beverage or a combination thereof.

5. The method of claim 4, wherein said method is a method for producing a beverage having stable organoleptic qualities, said method comprising:

(i) preparing a composition comprising the barley plant or a part thereof, (ii) processing the composition of (i) into a beverage; thereby obtaining a beverage with stable organoleptic qualities.

6. The method of claim 4, wherein (i) comprises preparing a malt composition from seeds of said barley plant or part thereof.

7. The method according to claim 4, wherein processing the composition into a beverages comprises a mashing step.

8. The method of claim 4, wherein said method is a method for producing a malt composition with no lipoxygenase-1 activity, said method comprising (i) providing seeds from the barley plant;

(ii) adding water to the seeds;

(iii) germinating the seeds from (ii); and (iv) treating germinated seeds with heat; thereby producing a malt composition.

9. The malt composition of claim 1, wherein the malt is produced from a part thereof and the part thereof is a seed.

10. The beverage of claim 3, which is beer.

* * * * *

SEQUENCE LISTING

```
<160> NUMBER OF SEQ ID NOS: 14

<210> SEQ ID NO 1
<211> LENGTH: 240
<212> TYPE: DNA
<213> ORGANISM: Hordeum vulgare

<400> SEQUENCE: 1

ctcgccaagg cctacgtcgc cgtcaatgac tccgggtggc accagctcgt cagccactgg     60

tacgttctcc acggtcgatg tgattcagtc agtcgatgca caacaactga tcgaaatatg    120

attgattgaa acgcgcaggc tgaacactca cgcggtgatg gagccgttcg tgatctcgac    180

gaaccggcac cttagcgtga cgcacccggt gcacaagctg ctgagcccgc actaccgcga    240


<210> SEQ ID NO 2
<211> LENGTH: 240
<212> TYPE: DNA
<213> ORGANISM: Hordeum vulgare

<400> SEQUENCE: 2

ctcgccaagg cctacgtcgc cgtcaatgac tccgggtggc accagctcgt cagccactga     60

tacgttctcc acggtcgatg tgattcagtc agtcgatgca caacaactga tcgaaatatg    120

attgattgaa acgcgcaggc tgaacactca cgcggtgatg gagccgttcg tgatctcgac    180

gaaccggcac cttagcgtga cgcacccggt gcacaagctg ctgagcccgc actaccgcga    240


<210> SEQ ID NO 3
<211> LENGTH: 24
<212> TYPE: DNA
<213> ORGANISM: Artificial
<220> FEATURE:
<223> OTHER INFORMATION: primer

<400> SEQUENCE: 3

ggagaggagg ccaagaacaa gatg                                            24


<210> SEQ ID NO 4
<211> LENGTH: 19
<212> TYPE: DNA
<213> ORGANISM: Artificial
<220> FEATURE:
<223> OTHER INFORMATION: primer

<400> SEQUENCE: 4

ggttgccgat ggcttagat                                                  19


<210> SEQ ID NO 5
<211> LENGTH: 21
<212> TYPE: DNA
<213> ORGANISM: Artificial
```

<220> FEATURE:
<223> OTHER INFORMATION: primer

<400> SEQUENCE: 5
cacgtcgccg tccgatccat c 21

<210> SEQ ID NO 6
<211> LENGTH: 20
<212> TYPE: DNA
<213> ORGANISM: Artificial
<220> FEATURE:
<223> OTHER INFORMATION: primer

<400> SEQUENCE: 6
ccatcacgca gggcatcctg 20

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
gcgttgatga gcgtctgccg 20

<210> SEQ ID NO 8
<211> LENGTH: 24
<212> TYPE: DNA
<213> ORGANISM: Artificial
<220> FEATURE:
<223> OTHER INFORMATION: primer for LOX-1 with BamHI site

<400> SEQUENCE: 8
ggatccatgc tgctgggagg gctg 24

<210> SEQ ID NO 9
<211> LENGTH: 25
<212> TYPE: DNA
<213> ORGANISM: Artificial
<220> FEATURE:
<223> OTHER INFORMATION: primer for LOX-1 with HindIII site

<400> SEQUENCE: 9
aagcttttag atggagatgc tgttg 25

<210> SEQ ID NO 10
<211> LENGTH: 2668
<212> TYPE: DNA
<213> ORGANISM: Hordeum vulgare

<400> SEQUENCE: 10
atgctgctgg gagggctgat cgacaccctc acgggggcga acaagagcgc ccggctcaag 60
ggcacggtgg tgctcatgcg caagaacgtg ctggacctca acgacttcgg cgccaccatc 120
atcgacggca tcggcgagtt cctcggcaag ggcgtcacct gccagcttat cagctccacc 180
gccgtcgacc aagacaacgg cggtcgcggg aaggtgggcg cggaggcgga gctggagcag 240
tgggtgacga gcctgccgtc gctgacgacg ggggagtcca agttcggcct caccttcgac 300
tgggaggtgg agaagctcgg ggtgccgggc gccatcgtcg tcaacaacta ccacagctcc 360
gagttcctgc ttaaaaccat caccctccac gacgtccccg gccgcagcgg caacctcacc 420
ttcgtcgcca actcatggat ctaccccgcc gccaactacc gatacagccg cgtcttcttc 480

-continued gccaacgaca cgtacctgcc gagccagatg ccggcggcgc tgaagccgta ccgcgacgac 540
gagctccgga acctgcgtgg cgacgaccag cagggcccgt accaggagca cgaccgcatc 600
taccgctacg acgtctacaa cgacctcggc gagggccgcc ccatcctcgg cggcaactcc 660
gaccaccctt acccgcgccg cggccgcacg gagcgcaagc ccaacgccag cgacccgagc 720
ctggagagcc ggctgtcgct gctggagcag atctacgtgc cgcgggacga gaagttcggc 780
cacctcaaga cgtccgactt cctgggctac tccatcaagg ccatcacgca gggcatcctg 840
ccggccgtgc gcacctacgt ggacaccacc cccggcgagt tcgactcctt ccaggacatc 900
atcaacctct atgagggcgg catcaagctg cccaaggtgg ccgccctgga ggagctccgt 960
aagcagttcc cgctccagct catcaaggac ctcctccccg tcggcggcga ctccctgctt 1020
aagctccccg tgccccacat catccaggag aacaagcagg cgtggaggac cgacgaggag 1080
ttcgcacggg aggtgctcgc cggcgtcaac ccggtcatga tcacgcgtct cacggagttc 1140
ccgccaaaaa gtagtctgga ccctagcaag tttggtgacc acaccagcac catcacggcg 1200
gagcacatag agaagaacct cgagggcctc acggtgcagc aggcgctgga aagcaacagg 1260
ctgtacatcc ttgatcacca tgaccggttc atgccgttcc tgatcgacgt caacaacctg 1320
cccggcaact tcatctacgc cacgaggacc ctcttcttcc tgcgcggcga cggcaggctc 1380
acgccgctcg ccatcgagct gagcgagccc atcatccagg gcggccttac cacggccaag 1440
agcaaggttt acacgccggt gcccagcggc tccgtcgaag gctgggtgtg ggagctcgcc 1500
aaggcctacg tcgccgtcaa tgactccggg tggcaccagc tcgtcagcca ctgatacgtt 1560
ctccacggtc gatgtgattc agtcagtcga tgcacaacaa ctgatcgaaa tatgattgat 1620
tgaaacgcgc aggctgaaca ctcacgcggt gatggagccg ttcgtgatct cgacgaaccg 1680
gcaccttagc gtgacgcacc cggtgcacaa gctgctgagc ccgcactacc gcgacaccat 1740
gaccatcaac gcgctggcgc ggcagacgct catcaacgcc ggcggcatct tcgagatgac 1800
ggtgttcccg ggcaagttcg cgttggggat gtcggccgtg gtgtacaagg actggaagtt 1860
caccgagcag ggactgccgg acgatctcat caagaggggc atggcggtgg aggacccgtc 1920
gagcccgtac aaggtgcggt tgctggtgtc ggactacccg tacgcggcgg acgggctggc 1980
gatctggcac gccattgagc agtacgtgag cgagtacctg gccatctact acccgaacga 2040
cggcgtgctg cagggcgata cggaggtgca ggcgtggtgg aaggagacgc gcgaggtcgg 2100
gcacggcgac ctcaaggacg ccccatggtg gcccaagatg caaagtgtgc cggagctggc 2160
caaggcgtgc accaccatca tctggatcgg gtcggcgctg catgcggcag tcaacttcgg 2220
gcagtacccc tacgcggggt tcctcccgaa ccggccgacg gtgagccggc gccgcatgcc 2280
ggagcccggc acggaggagt acgcggagct ggagcgcgac ccggagcggg ccttcatcca 2340
caccatcacg agccagatcc agaccatcat cggcgtgtcg ctgctggagg tgctgtcgaa 2400
gcactcctcc gacgagctgt acctcgggca gcgggacacg ccggagtgga cctcggaccc 2460
aaaggccctg gaggtgttca agcggttcag cgaccggctg gtggagatcg agagcaaggt 2520
ggtgggcatg aaccatgacc cggagctcaa gaaccgcaac ggcccggcta agtttcccta 2580
catgctgctc taccccaaca cctccgacca caagggcgcc gctgccgggc ttaccgccaa 2640
gggcatcccc aacagcatct ccatctaa 2668

<210> SEQ ID NO 11
<211> LENGTH: 4393
<212> TYPE: DNA
<213> ORGANISM: Hordeum vulgare -continued

<400> SEQUENCE: 11

```
cacgtcgccg tccgatccat ctctccaaag ccgagcgcca caccaccggg accggacccg     60
gaccggccta taaattgccc ggaccgagct gcaagcagct cctcacacac actcacgcaa    120
cacacatcca tcttcactga aaagtgaaaa acagtgtgct ggtgccattg gttggagcag    180
tgaaagcgag gagaggaggc caagaacaag atgctgctgg gagggctgat cgacaccctc    240
acgggggcga acaagagcgc ccggctcaag ggcacggtgg tgctcatgcg caagaacgtg    300
ctggacctca acgacttcgg cgccaccatc atcgacggca tcggcgagtt cctcggcaag    360
ggcgtcacct gccagcttat cagctccacc gccgtcgacc aaggtaatca ctaccctcct    420
ccggccttct cctctgttta caagatatag tatttctttc gtgtgggccg gcggccatgg    480
atggatggat gtgtctggat cggctaaaga agataggata gctagccctg gccggtcgtc    540
tttacctgag catgggcata tgccatcgaa aaaagagaca acagcatgca tgcatggtgc    600
gcgcaccaga ccacgcagag caccggatgc tcgagacaaa gcaacacaac aagcaaggac    660
gacacgtcaa aagcaacaca acaagcaagg acggcacgtc aaaagcaaca caaacctaaa    720
ctaaagcaca aagacgtaag agcaagcaca caatcagcag gctataaaca gttgtcatca    780
aaaacaacgc tggaagagag agagaaggaa ggaagtagta gccatgaaaa attaaatcac    840
cgggcgttgc tctttgccca acaattaatc aagcagggta cgtggcatgt atagttcttg    900
taagtaaact aagcatgtga tatgagaagg tacgtggtgg tgcagacaac ggcggtcgcg    960
ggaaggtggg cgcggaggcg gagctggagc agtgggtgac gagcctgccg tcgctgacga   1020
cgggggagtc caagttcggc ctcaccttcg actgggaggt ggagaagctc ggggtgccgg   1080
gcgccatcgt cgtcaacaac taccacagct ccgagttcct gcttaaaacc atcaccctcc   1140
acgacgtccc cggccgcagc ggcaacctca ccttcgtcgc caactcatgg atctaccccg   1200
ccgccaacta ccgatacagc cgcgtcttct tcgccaacga cgtgcgtgga ttttcctcta   1260
ctttcctctc ctttcatttt caccgccttc gtcattcatg gtcgatcatt aagtcttgcc   1320
aggacaatag atgatgagct aggagtggtt accacttagc agtacgtaca ttatttattc   1380
cgtgttggta gaaaaggata tggtttggtg cagatcgaca caagattgaa tgaaagttgc   1440
accgtggcac cgtggcagcg tggtaggtga aaataactgt tgcacggatc cacccacatg   1500
attgttttca tgaataaact ttttaaggat gtgtctagcc acatctagat gcatgtcaca   1560
taattattgc ataccaaaac gattaaatta agcataaaaa gaaaaggaaa aaaatactca   1620
catatctcga cgtaagatca atgatatagt atttagatat gcaatattta tcttacatct   1680
aaacctttct tcattcctaa atataagaca tttgtaagat ttcactatgg acaacatacg   1740
aaacaaaatc agtggatctc tctatgcatt cattatgtag tctataataa aatctttaaa   1800
agatcgtata ttttgcaacg gagggagtaa aacataactt tttaatagta atgttgcacg   1860
gctccacact cgcagacgta cctgccgagc cagatgccgg cggcgctgaa gccgtaccgc   1920
gacgacgagc tccggaacct gcgtggcgac gaccagcagg gcccgtacca ggagcacgac   1980
cgcatctacc gctacgacgt ctacaacgac ctcggcgagg gccgccccat cctcggcggc   2040
aactccgacc acccttaccc gcgccgcggc cgcacggagc gcaagcccaa cgccagcgac   2100
ccgagcctgg agagccggct gtcgctgctg gagcagatct acgtgccgcg ggacgagaag   2160
ttcggccacc tcaagacgtc cgacttcctg ggctactcca tcaaggccat cacgcagggc   2220
atcctgccgg ccgtgcgcac ctacgtggac accacccccg gcgagttcga ctccttccag   2280
```

-continued

```
gacatcatca acctctatga gggcggcatc aagctgccca aggtggccgc cctggaggag   2340
ctccgtaagc agttcccgct ccagctcatc aaggacctcc tccccgtcgg cggcgactcc   2400
ctgcttaagc tccccgtgcc ccacatcatc caggagaaca agcaggcgtg gaggaccgac   2460
gaggagttcg cacgggaggt gctcgccggc gtcaacccgg tcatgatcac gcgtctcacg   2520
gtgagtcagc gattatttgt tcattgtgtg tgtatggtgt ccatggtgag aaagtgcaga   2580
tcttgatttg cgttgggtcg catgcacgca tgctgcatgc atgcaggagt tcccgccaaa   2640
aagtagtctg gaccctagca agtttggtga ccacaccagc accatcacgg cggagcacat   2700
agagaagaac ctcgagggcc tcacggtgca gcaggtaatt ggtccaagcc atcgacatca   2760
actatgattt acctaggagt aattggtagc tgtagataat ttggcttcgt tgcaattaat   2820
ttgatgctgg ccgatcaagt gatcgtattg ggtttgaaat ttgcaggcgc tggaaagcaa   2880
caggctgtac atccttgatc accatgaccg gttcatgccg ttcctgatcg acgtcaacaa   2940
cctgcccggc aacttcatct acgccacgag gaccctcttc ttcctgcgcg gcgacggcag   3000
gctcacgccg ctcgccatcg agctgagcga gcccatcatc cagggcggcc ttaccacggc   3060
caagagcaag gtttacacgc cggtgcccag cggctccgtc gaaggctggg tgtgggagct   3120
cgccaaggcc tacgtcgccg tcaatgactc cgggtggcac cagctcgtca gccactgata   3180
cgttctccac ggtcgatgtg attcagtcag tcgatgcaca acaactgatc gaaatatgat   3240
tgattgaaac gcgcaggctg aacactcacg cggtgatgga gccgttcgtg atctcgacga   3300
accggcacct tagcgtgacg cacccggtgc acaagctgct gagcccgcac taccgcgaca   3360
ccatgaccat caacgcgctg gcgcggcaga cgctcatcaa cgccggcggc atcttcgaga   3420
tgacggtgtt cccgggcaag ttcgcgttgg ggatgtcggc cgtggtgtac aaggactgga   3480
agttcaccga gcagggactg ccggacgatc tcatcaagag gtacgtacct ggtaaatgtt   3540
atgaatgtgt aaaacaaatt gggcgtctcg ctcactgaca ggaacgtggt aaaaaaaatg   3600
caggggcatg gcggtggagg acccgtcgag cccgtacaag gtgcggttgc tggtgtcgga   3660
ctacccgtac gcggcggacg ggctggcgat ctggcacgcc attgagcagt acgtgagcga   3720
gtacctggcc atctactacc cgaacgacgg cgtgctgcag ggcgatacgg aggtgcaggc   3780
gtggtggaag gagacgcgcg aggtcgggca cggcgacctc aaggacgccc catggtggcc   3840
caagatgcaa agtgtgccgg agctggccaa ggcgtgcacc accatcatct ggatcgggtc   3900
ggcgctgcat gcggcagtca acttcgggca gtacccctac gcggggttcc tcccgaaccg   3960
gccgacggtg agccggcgcc gcatgccgga gcccggcacg gaggagtacg cggagctgga   4020
gcgcgacccg gagcgggcct tcatccacac catcacgagc cagatccaga ccatcatcgg   4080
cgtgtcgctg ctggaggtgc tgtcgaagca ctcctccgac gagctgtacc tcgggcagcg   4140
ggacacgccg gagtggacct cggacccaaa ggccctggag gtgttcaagc ggttcagcga   4200
ccggctggtg gagatcgaga gcaaggtggt gggcatgaac catgacccgg agctcaagaa   4260
ccgcaacggc ccggctaagt ttccctacat gctgctctac cccaacacct ccgaccacaa   4320
gggcgccgct gccgggctta ccgccaaggg catccccaac agcatctcca tctaatttaa   4380
gccatcggca acc                                                      4393
```

<210> SEQ ID NO 12
<211> LENGTH: 60
<212> TYPE: DNA
<213> ORGANISM: Hordeum vulgare
<220> FEATURE:
<221> NAME/KEY: misc_feature -continued

```
<222> LOCATION: (30)..(30)
<223> OTHER INFORMATION: G in the authentic LOX-1 gene

<400> SEQUENCE: 12

tccgggtggc accagctcgt cagccactgg tacgttctcc acggtcgatg tgattcagtc     60


<210> SEQ ID NO 13
<211> LENGTH: 60
<212> TYPE: DNA
<213> ORGANISM: Hordeum vulgare
<220> FEATURE:
<221> NAME/KEY: misc_feature
<222> LOCATION: (30)..(30)
<223> OTHER INFORMATION: A in the mutant LOX-1 gene

<400> SEQUENCE: 13

tccgggtggc accagctcgt cagccactga tacgttctcc acggtcgatg tgattcagtc     60


<210> SEQ ID NO 14
<211> LENGTH: 9
<212> TYPE: PRT
<213> ORGANISM: Hordeum vulgare

<400> SEQUENCE: 14

Ser Gly Trp His Gln Leu Val Ser His
1               5
```